(12) United States Patent
Tajima

(10) Patent No.: US 8,696,992 B2
(45) Date of Patent: Apr. 15, 2014

(54) OPTICAL FIBER MEASUREMENT DEVICE AND MEASUREMENT METHOD USING SAME

(75) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 122 days.

(21) Appl. No.: 13/388,885

(22) PCT Filed: Aug. 5, 2010

(86) PCT No.: PCT/JP2010/063267
§ 371 (c)(1),
(2), (4) Date: Apr. 11, 2012

(87) PCT Pub. No.: WO2011/016509
PCT Pub. Date: Feb. 10, 2011

(65) Prior Publication Data
US 2012/0190034 A1    Jul. 26, 2012

(30) Foreign Application Priority Data
Aug. 6, 2009   (JP) .................................. 2009-183819

(51) Int. Cl.
| | | |
|---|---|---|
| G01N 21/00 | (2006.01) | |
| G01N 21/76 | (2006.01) | |
| C12M 1/34 | (2006.01) | |
| G01N 21/25 | (2006.01) | |

(52) U.S. Cl.
USPC .................. 422/82.05; 422/82.08; 422/82.11; 435/287.2; 436/164; 436/172; 356/318; 356/417

(58) Field of Classification Search
None
See application file for complete search history.

(56) References Cited

U.S. PATENT DOCUMENTS 5,589,351 A * 12/1996 Harootunian .................... 435/29
6,187,267 B1 * 2/2001 Taylor et al. ..................... 422/52
6,448,089 B1    9/2002 Vuong

FOREIGN PATENT DOCUMENTS

| JP | 10-510049 | 9/1998 |
|---|---|---|
| JP | 10-281994 | 10/1998 |

(Continued)

OTHER PUBLICATIONS

International Search Report mailed Nov. 9, 2010, by the ISA/JP regarding Int'l App No. PCT/JP2010/063267.

(Continued)

Primary Examiner — Neil N Turk
(74) Attorney, Agent, or Firm — Haynes and Boone, LLP

(57) ABSTRACT

Disclosed is a highly reliable optical fiber measurement device and measurement method having a simple and compact structure. The device includes a planar liquid holder having a plurality of liquid holding portions arranged along a flat face; a plurality of light receiving optical fibers for transmitting fluorescence generated in the liquid holding portions; a plurality of light emitting optical fibers for transmitting excitation light into the liquid holding portions; a measurement head capable of being positioned in the each liquid holding portion while supporting a plurality of measurement ends having a bundle of one light receiving end of the light receiving optical fibers and one light emitting end of light emitting optical fibers; a light reception selecting element that, by sequentially selecting one by one from plural the light receiving optical fibers and sequentially selecting one by one from plural kinds of wavelength or wavelength bands, sequentially guides the light of the selected wavelength or wavelength band of the fluorescence received by the selected light receiving optical fibers to one photoelectric element; and a photoelectric element for sequentially conducting photoelectric conversion on the guided fluorescence.

8 Claims, 14 Drawing Sheets

(56) References Cited

FOREIGN PATENT DOCUMENTS

| JP | 2002-509235 | 3/2002 |
| JP | 2003-511702 | 3/2003 |
| JP | 2007-205774 | 8/2007 |
| JP | 2008-261842 | 10/2008 |

OTHER PUBLICATIONS

Written Opinion mailed Nov. 9, 2010, by the ISA/JP regarding Int'l App No. PCT/JP2010/063267.
International Preliminary Examination Report on mailed Oct. 18, 2011, by the ISA/JP regarding Int'l App No. PCT/JP2010/063267.

* cited by examiner

Fig. 4

| No. | DEGREE | OPTICAL FIBER | OPTICAL FILTER |
|---|---|---|---|
| 1 | 0 | a | 561 |
| 2 | 20 | c | 562 |
| 3 | 40 | e | 563 |
| 4 | 60 | b | 561 |
| 5 | 80 | d | 562 |
| 6 | 100 | f | 563 |
| 7 | 120 | c | 561 |
| 8 | 140 | e | 562 |
| 9 | 160 | a | 563 |
| 10 | 180 | d | 561 |
| 11 | 200 | f | 562 |
| 12 | 220 | b | 563 |
| 13 | 240 | e | 561 |
| 14 | 260 | a | 562 |
| 15 | 280 | c | 563 |
| 16 | 300 | f | 561 |
| 17 | 320 | b | 562 |
| 18 | 340 | d | 563 |

OPTICAL FIBER MEASUREMENT DEVICE AND MEASUREMENT METHOD USING SAME

CROSS REFERENCE

This application is a United States national phase application of co-pending international patent application number PCT/JP2010/063267, filed Aug. 5, 2010, which claims priority to Japanese patent application number 2009-183819, filed Aug. 6, 2009, the disclosures of which are incorporated herein by reference.

TECHNICAL FIELD

The present invention relates to an optical fiber measurement device and a measurement method using the same.

BACKGROUND ART

In recent years, it is widely conducted to obtain various information by measuring plural kinds of fluorescent substances for a reaction in a solution containing biological substances such as DNA, protein, lipid, and sugar labeled with plural kinds of fluorescent substances. One exemplary case includes labeling various DNA fragments having unknown nucleotide sequences with plural kinds of fluorescence, and measuring a binding state with a DNA fragment having a known nucleotide sequence that is solid-phased to a DNA chip or the like and complementarily binding thereto. Another example is application to a real-time PCR or the like that monitors nucleic acid (DNA) amplified by PCR in real time by utilizing a fluorescent substance.

The real-time PCR is advantageous in that amplification can be measured even in the course of temperature cycle and a quantitative result is obtained, and by detecting and analyzing a course of generation of an amplified product labeled with a fluorescent substance in PCR in real time, it is possible to conduct quantification more accurately. As a typical method conducted by using a fluorescent reagent containing a fluorescent substance, an intercalation method, a hybridization method and a LUX method are recited.

The "intercalation method" is a method of measuring a DNA amount utilizing the nature of a fluorescent substance such as SYBR (trademark) GREEN I, or ethidium bromide of breaking into double-stranded DNA during an elongation reaction, and generating fluorescence in response to emission of excitation light. The "hybridization method" is a method of detecting only a target PCR product using a DNA probe labeled with a fluorescent substance in addition to a PCR primer. In other words, by hybridization of a DNA probe labeled with fluorescence, with a target PCR product, the hybridized DNA (amount) is detected. The "LUX method" utilizes the property that a fluorescent signal of a fluorescent substance labeling oligo nucleic acid is influenced by the form (sequence, single strand or double strand, and so on) of the oligo nucleic acid. In an actual real time PCR, real time PCR is executed using a PCR primer labeled with one kind of fluorescent substance (LUX primer) and an unlabeled PCR corresponding to the same. The LUX primer is labeled with a fluorescent substance near 3' terminal, and is designed to assume a hairpin structure with 5' terminal. When the LUX primer assumes a hairpin structure, the quenching effect is canceled and the fluorescent signal increases. By measuring the signal increase, an amount of the PCR product can be measured.

For making such accurate quantitative measurement possible, more accurate and rapid optical measurement is required, and various devices have been developed for that. An optical fiber bundle is provided for each well, and part of optical fibers of the optical fiber bundle are used for emission of excitation light, and the remaining optical fibers are used for guiding fluorescence to a light receiving part. It is also proposed to provide the optical fiber bundle to be sequentially movable for each well (Patent Literature 1).

CITATION LIST

Patent Literature

Patent Literature 1: U.S. Pat. No. 6,448,089

SUMMARY OF INVENTION

Technical Problem

However, for example, when real time PCR measurement is conducted for a plurality of samples or targets, it is necessary to label with fluorescent substances having different wavelengths, and a plurality of photomultipliers corresponding to respective wavelengths are used. Therefore, the numbers of light sources for excitation light and photomultipliers increase, and a complicated optical system is required for branching fluorescence transmitted from a reaction container, and the structure of the device is complicated, and the device scale is increased, so that there is a fear of increased production cost. Further, measuring for each well one by one is problematic because of poor processing efficiency and consumption of time.

The present invention was devised to solve the aforementioned problems, and the first object of the invention is to provide an optical fiber measurement device and a measurement method thereof capable of conducting measurement of reactions of various biochemical substances labeled with plural kinds of fluorescent substances, for example, measurement of real time PCR regarding DNA or the like, for a plurality of liquid holding portions holding these, without using a complicated optical system, and the second object of the invention is to provide an optical fiber measurement device and a measurement method thereof that is easy to be adjusted and easy to be used. The third object of the invention is to provide a highly reliable optical fiber measurement device and a measurement method thereof.

Solution to Problem

The first aspect of the invention is an optical fiber measurement device comprising: a planar liquid holder having a plurality of liquid holding portions capable of holding a reaction solution containing a fluorescent substance arranged along a flat face; a plurality of light receiving optical fibers for transmitting fluorescence generated in the liquid holding portions; a plurality of light emitting optical fibers for transmitting excitation light into the liquid holding portions; a measurement head capable of being positioned in the entire or part of the plurality of liquid holding portions of the planer liquid holder while supporting a plurality of measurement ends having a bundle of one light receiving end of the light receiving optical fibers receiving the fluorescence and one or two or more light emitting ends of the light emitting optical fibers emitting the excitation light; a light reception selecting element that, by sequentially selecting one by one from plural the light receiving optical fibers and sequentially selecting one by one from plural kinds of wavelength or wavelength bands, sequentially guides light of the selected wavelength or wavelength band of the fluorescence received by the selected light receiving optical fibers to one photoelectric element; and a photoelectric element for sequentially conducting photoelectric conversion on the fluorescence that is selected by the light reception selecting element and guided.

Here, the "reaction solution" is a solution where reaction of a biological substance, for example, PCR or the like reaction is conducted, and is a solution containing, for example, template DNA, primer, DNA polymerase, nucleotide, a reaction buffer liquid and so on.

The "liquid holding portion" is a portion capable of holding, reserving or retaining a liquid, and is, for example, a well, a container, or a tube. The "planner liquid holder" is a micro plate where the wells are arranged in a planar form, for example, in a matrix form, a cartridge container where the wells are arranged in a column form or in a row form, or a tube support or a container support where a plurality of tubes or containers are inserted and supported in holes and so on arranged in planar form including a column form and a row form. Further, not only those having an apparent container shape, but also the one where a spot-like liquid on a chip such as DNA chip is held in a plurality of arranged recesses, and the case where infiltrated or placed in a infiltration spot where liquid infiltration is possible are included. The micro plate includes, for example, ninety-six wells of 9 mm pitch arranged in the matrix of eight rows×twelve columns.

In the "planar liquid holder", for preventing evaporation or the like of a liquid and allowing optical measurement while the liquid is held, it is preferred that the liquid holding portions such as all wells, all tubes or all container provided in the planar liquid holder are covered, for example, with a transparent thin film to block the opening.

The "planar liquid holder" includes, for example, the case where a plurality of the liquid holding portions are arranged in the form of a matrix. In this case, the wording of part of the planar liquid holder means, for example, one row, one column, several columns, or several rows of the liquid holding portions arranged in the form of a matrix, and may be a matrix of several rows×several columns using a divisor of the row number or column number.

The "measurement end" preferably has such a size or shape that when it is positioned above one of the liquid holding portions, it allows incidence of light radiated in a vertical direction from an opening of the liquid holding portion and guides it to the light receiving optical fibers while not allowing incidence of light from an opening of other liquid holding portion. For achieving this, it is preferred to have a measurement end larger than the diameter of the opening, but has such a diameter that will not reach an opening of other liquid holding portion possibly emitting fluorescence. In that case, as a measurement end, it is preferred to provide an optical system such as a focused parallel light lens having such a diameter in front of a bundle of the light emitting optical fiber and light receiving optical fiber, and allow received light enter parallel with the light receiving optical fiber while allowing excitation light emit parallel from the light emitting optical fiber. When the measurement end is formed to be larger than an opening of the liquid holding portion, and the size of the measurement end is larger than the pitch between the liquid holding portions, the pitch between the measurement ends may be set at a natural number (excluding 1) times the pitch between the liquid holding portions. Alternatively, the measurement end may be arranged in a zigzag alignment rather than in one column (one row) array.

Not only the case where temperature control is conducted in the liquid holding portion, but also the case where temperature control is not conducted in the liquid holding portion are included. Here, the "temperature control" means executing retention of an objective liquid or container at one or two or more predetermined temperatures for a specified time, for example, by the order determined by a PCR method or the like, predetermined times. Instruction of the temperature control is made by sending a corresponding signal based on a program.

The "temperature control" is executed by providing the planar liquid holder with a metal block provided with a temperature source capable of increasing or decreasing the temperature of the liquid holding portion holding a liquid which is an object to be controlled according to an external signal or the like, and as the temperature source, for example, a Peltier device, a heater, a cooling device and the like are recited.

The "predetermined temperature" is a target temperature that the objective matter such as a liquid is to reach, and for example, when nucleic acid, oligonucleotide and the like such as DNA contained in the liquid is amplified by the PCR method, the predetermined temperature to be set includes, for example, a temperature cycle conducted in the PCR method, concretely, various temperatures necessary for thermal denaturation, annealing or hybridization, and elongation of DNA, about 94° C., a temperature from 50° C. to 60° C., for example, about 50° C., and about 72° C. Further, the predetermined temperature includes a transition promoting temperature for shortening the transition time and making one cycle time fall within predetermined cycle time, by conducting, in transition from a higher predetermined temperature to a lower predetermined temperature, cooling at a transition promoting temperature lower than these predetermined temperatures, or by conducting, in transition from a lower predetermined temperature to a higher predetermined temperature, heating at a transition promoting temperature higher than these predetermined temperatures by a temperature controller. The "predetermined time" is a time required for maintaining each temperature, and the total is, for example, several seconds to several tens seconds in one cycle, and the processing time as the entire PCR method is, for example, about several minutes to several tens minutes although it depends on a reagent or a liquid amount, shape, material, size, thickness and the like of nozzle used in the PCR method. The transition time is also included in the predetermined time.

The "photoelectric element" is an electronic element utilizing a photoelectric effect, and includes a phototube, photomultiplier, photoconductive cell, phototransistor, and photodiode.

The second aspect of the invention is an optical fiber measurement device, wherein the light reception selecting element has: a connecting end arrangement plate supporting a plurality of connecting ends on the opposite side of the light receiving ends of the light receiving optical fibers arranged along a circumference at a predetermined central angle; a light receiving rotary plate provided oppositely, closely to the connecting end arrangement plate and provided to be rotatable concentrically with the circumference of the connecting end arrangement plate; a plurality of optical filters that are arranged on the light receiving rotary plate at a predetermined central angle along a circumference that has a same diameter with the circumference of the connecting end arrangement plate and is concentric therewith, and are optically connectable one by one with each connecting end by rotation of the light receiving rotary plate; and a light receiving optical system provided in the light receiving rotary plate, for allowing light passing the each optical filter independently enter a central axis region of the light receiving rotary plate, and the photoelectric element is provided to allow introduction of the light entering the central axis region.

For making "optically connectable to each connecting end one by one by rotation of the light receiving rotary plate", as each "predetermined central angle", it is necessary to determine the central angle between neighboring optical filters so that any two or more optical filters and any two or more the connecting ends will not connect concurrently by overlapping in the axial direction by rotation of the light receiving rotary plate. The "oppositely, closely" means that opposing surfaces are in such a close relation that they do not contact each other, and are away from each other to such a degree that at least one is rotatable with respect to the other, and when ends of respectively arranged optical paths are at the closest positions, the entire or most of the light from one of the ends (for example, the connecting end) is emitted on the other end (for example, the optical filter), but not on other ends, and means the case, for example, the distance between the connecting end arrangement plate and the light receiving rotary plate is about 0.1 mm to about 100 mm although it differs depending on the distance between ends arranged on the same surface or the like. Since it is "light receiving rotary plate provided to be rotatable concentrically with the circumference of the connecting end arrangement plate", the rotation axial line of the light receiving rotary plate is provided concentrically with the circumference, and coincides with the central axis of the connecting end arrangement plate.

For achieving this, for example, when the number of connecting ends is n, the central angle $\alpha$ of neighboring connecting ends is an angle obtainable by dividing 360 degrees equally into n, the number of optical filters is m, and the neighboring central angles are $\theta_1, \ldots \theta_m$, $n \times \alpha = 360$ degrees, and $\theta_1 + \theta_2 + \ldots + \theta_m = 360$ degrees are established (conversely, when the central angle $\alpha$ of neighboring optical filters is an angle obtainable by dividing 360 degrees equally into m, and the neighboring central angles of connecting ends are $\theta_1, \ldots \theta_n$, $m \times \alpha = 360$ degrees, and $\theta_1 + \theta_2 + \ldots + \theta_n = 360$ degrees are established). In this case, for making the optical filters be optically connectable with the each connecting ends one by one, the requirement should be imposed that each central angle $\theta_1, \ldots \theta_m$ and a sum of neighboring any number of central angles are not equal to or a natural number times of the central angle $\alpha$ of neighboring connecting ends.

When the connecting end and the optical filter are connected with each other, it is necessary to stop for a predetermined connecting time (for example, in the order of several tens milliseconds, sensed by the photoelectric element, the time needed for the process). In other words, rotation is intermittent rotation rather than continuous rotation. On the other hand, assuming that the life time of fluorescence is in the order in about several seconds by emission of excitation light, it is preferred that the rotation speed of the light receiving rotary plate is set so that the rotary plate can rotate around (for example, several seconds for one cycle) within a time not exceeding the life time of the fluorescence while considering the predetermined connecting time.

The "light receiving optical systems" includes two mirrors provided so that light travels along the radial direction of the light receiving rotary plate, a reflecting prism provided with two reflecting surfaces so that light travels along its radial direction, and a combination of a mirror and a prism. Generally, a mirror can realize reduced weight compared with a reflecting prism. When two mirrors are used or when a reflecting prism provided with two reflecting surfaces is used, one mirror or one of the reflecting surfaces is provided so that the normal direction of the mirror surface or the reflecting surface of the reflecting prism forms 45 degrees or 135 degrees with respect to the normal direction of the each optical filter surface or light receiving rotary plate so that the light from the connecting end enters at an incidence angle of 45 degrees and travels along the radial direction, and the light passing through the optical filter from the connecting end is allowed to travel along the radial direction of the light receiving rotary plate, and the other mirror or the other reflecting surface is provided near the central axis of the light receiving rotary plate, and is provided to reflect the light reflected by the mirror or the reflecting surface and traveling in the radial direction at such an angle that allows incidence in the central axis region. As a result, the light outgoing from the mirror or the reflecting prism can be securely introduced into the photoelectric element. It is necessary that the m light receiving optical systems have the same structure.

The "optical filter" is provided for extracting light of a predetermined wavelength or wavelength band from incidence light. The optical filter is provided, for example, for allowing passage of a wavelength of light of the kind labeling a DNA fragment or the like for which quantity or concentration is to be measured by real time PCR, while preventing transmission of light having other wavelength. When a labeling substance that outputs plural kinds of light wavelengths is used, it is possible to measure the existence or quantity of the labeling substance by providing plural kinds of optical filters and allowing light having a particular wavelength to pass through the respective optical filter.

The "plural optical filters" are, for example, plural kinds of optical filters capable of respectively allowing transmission of lights of different wavelength or wavelength bands.

The light receiving end, light emitting end, or connecting end is formed with a lens, and is preferably provided with a lens or a lens system.

The expression "the light having passed each optical filter is independently allowed to enter the central axis region of the light receiving rotary plate" means that light is allowed to enter the central axis region of the light receiving rotary plate while the paths of light passing the respective optical filters do not overlap with each other.

Here, the "central axis region" is a planar region where the central axis (coincidence with the rotation axial line) of the light receiving rotary plate penetrates through, having a certain area in the direction perpendicular to the central axis, and is such a region that the light entering this can be introduced into the photoelectric element. In a typical case, the central axis region is provided with an incidence end face that is perpendicular to the direction of the central axis of the photoelectric element. In another case, a lens surface of an optical system is provided so that the light entering therein enters the incidence end face of the photoelectric element.

The "photoelectric element" is preferably fixedly provided separately from the light receiving rotary plate so that the normal line of its incidence end face is directed to the central axis of the light receiving rotary plate.

The third aspect of the invention is an optical fiber measurement device, wherein the central angle of the connecting end and the central angle of the optical filter are defined so that during rotation of a total of 360 degrees by repetition of rotation in a constant direction by an equivalent angle of the light receiving rotary plate and stopping for a predetermined connecting time, every combination of all of the connecting ends provided in the connecting end arrangement plate and all of the optical filters provided in the light receiving rotary plate is optically connected one by one for the predetermined connecting time, and the light having passed both the connecting end and the optical filter is guided to the photoelectric element.

Since all combinations of connecting ends and optical filters are realized eventually by rotation of 360 degrees of the rotary plate by repeating rotation in a certain direction at an equivalent angle β of the rotary plate and stopping for the predetermined connecting time, it is necessary that m×n×β=360 degrees. Therefore, m×β=α.

For example, when the number m of optical filters is three, and the number n of connecting ends (light receiving optical fibers) is six, α=60 degrees, and hence it is necessary that β=20 degrees. Since respective central angles $\theta_1$, $\theta_2$, $\theta_3$ should be formed by 20 degrees as a unit, it can be described by $\theta_1=20\times\phi_1$, $\theta_2=20\times\phi_2$, $\theta_3=20\times\phi_3$, and natural numbers $\phi_1$, $\phi_2$, $\phi_3$ should be determined so that $\phi_1+\phi_2+\phi_3=18$, and $\phi_1$, $\phi_2$, $\phi_3$, and $\phi_1+\phi_2$, $\phi_2+\phi_3$, $\phi_1+\phi_3$ are not multiples of three.

Therefore, when the number m of optical filters is three, and the number n of connecting ends is six, there are only eight combinations of $(\phi_1, \phi_2, \phi_3)$=(1, 1, 16), (1, 4, 13), (1, 7, 10), (2, 5, 11), (2, 8, 8), (4, 4, 10), (4, 7, 7), (5, 5, 8). Therefore, as central angle $(\theta_1, \theta_2, \theta_3)$ between neighboring the optical filters, eight kinds of neighboring central angles of (20, 20, 320), (20, 80, 260), (20, 140, 200), (40, 100, 220), (40, 160, 160), (80, 80, 200), (80, 140, 140), (100, 100, 160), or combinations of central angles having different permutations of these are obtained by multiplying the $(\phi_1, \phi_2, \phi_3)$ by respectively 20 degrees.

In this case, considering central angles of the connecting end and optical filter themselves and diameter of the circumference, they should be determined so that they do not overlap with each other. Further, the each light receiving optical system is the light receiving rotary plate, and need to have such a size formable in the neighboring central angle. Also when m and n are other numerical values, α, β and $\theta_1, \ldots \theta_m$ can be derived by using the foregoing mathematical formula.

The fourth aspect of the invention is an optical fiber measurement device, wherein the light reception selecting element has: a connecting end arrangement plate supporting a plurality of connecting ends on the opposite side of the light receiving ends of the light receiving optical fibers arranged along a circumference; a light guiding rotary plate for light reception selection provided oppositely to the connecting end arrangement plate, and provided to be rotatable concentrically with the circumference of the connecting end arrangement plate, for sequentially guiding light entered from the connecting ends to outgo approximately along its rotation axial line; and an optical filter arrangement plate having a plurality of optical filters provided movably with respect to the rotation axial line so that the light outgoing from the light guiding rotary plate can sequentially enter, and the photoelectric element is provided to allow introduction of the light passed through the optical fibers.

Here, the light receiving rotary plate, light guiding rotary plate, or optical filter arrangement plate may be manually driven rather than by a motor. In the case of manual drive, the device structure is simplified. The movement of "optical filter arrangement plate" is a rotation movement that is concentric with a circumference intersecting with the rotation axial line of the light guiding rotary plate at right angle, along which optical filters are arranged. The "light guiding rotary plate" guides on a rotary plate, the light entering at an incidence point apart from its rotation center to the rotation center, and outputs the light guided to the rotation center approximately along the rotation axial line. Therefore, when the end of the optical fiber provided oppositely closely to the rotation axis or the light source provided oppositely to the rotary plate is arranged on a circumference passing the incidence point, it is possible to sequentially output light approximately along the rotation axial line by rotation.

The fifth aspect of the invention is an optical fiber measurement device, wherein during rotation of a total of 360 degrees by repetition of rotation in a constant direction by every predetermined central angle of the light guiding rotary plate and stopping for a predetermined connecting time, every combination of all of the connecting ends provided in the connecting end arrangement plate and all of the optical filters provided in the optical filter arrangement plate is optically connected one by one for the predetermined connecting time, and the light having passed both the connecting end and the optical filter is guided to the photoelectric element. Here, the "predetermined central angle" includes the case where it is a central angle of equivalent angle.

The sixth aspect of the invention is an optical fiber measurement device, further comprising a shifting mechanism that allows relative movement between the measurement head supporting the measurement ends and the planar liquid holder. Here, since the movement is "relative", the case of shifting the measurement head and the case of shifting the planar liquid holder are included.

The seventh aspect of the invention is an optical fiber measurement device, comprising an exciting light source selecting element, for selecting light from a light source for the excitation light and guiding it to connecting ends on the opposite side of the light emitting ends of one or two or more the light emitting optical fibers. Here, in guiding the light from the exciting light source to the light emitting optical fiber, it may be passed through a predetermined optical filter.

The eighth aspect of the invention is an optical fiber measurement device, wherein the exciting light source selecting element has: an exciting light source arrangement plate provided with arranged plural kinds of exciting light sources; a light source selecting part for selecting one of the exciting light sources arranged in the exciting light source arrangement plate; and a light emitting optical system for guiding light from the exciting light source selected by the light source selecting part to one or two or more bundles of the connecting ends on the opposite side of the light emitting ends of the light emitting exciting optical fibers.

Here, as the "exciting light source", a bulb-type light source such as a xenon lamp or a halogen lamp, a plurality of light emitting elements of the number according to the number of liquid holding portions to be irradiated, or the kind or number of wavelengths, for example, an array-like light source in which super luminosity LEDs are arranged, a line-like light source, and a planar light source are recited. As the "light emitting optical system", for example a lens for focusing parallel light such as, for example, a compound lens is recited.

The light from the exciting light source may be guided to a connecting end after it has passed through a predetermined optical filter. When there are many kinds of light sources and many kinds of optical filters that allow passing of the light from a light source, the one in which as the exciting light source arrangement plate, an exciting light source is arranged in place of the connecting end in the connecting end arrangement plate, and as the light source selecting part, the optical filter in the light receiving rotary plate is replaced by an appropriate one may be used.

Alternatively, as will be described later, a light guiding rotary plate for light source selection may be used.

The ninth aspect of the invention is an optical fiber measurement device, wherein the exciting light source arrangement plate supports a plurality of exciting light sources arranged along a circumference at a predetermined central angle, the light source selecting part and light emitting optical system are a light guiding rotary plate for light source selection that is provided oppositely to the exciting light source arrangement plate and provided to be rotatable concentrically with the circumference of the exciting light source arrangement plate, and guides the light entered from the light source to outgo approximately along its rotation axial line, and the bundles of the connecting ends of the light emitting optical fibers are provided so that the rotation axial line penetrates therethrough.

The tenth aspect of the invention is an optical fiber measurement device, wherein the exciting light source arrangement plate supports a plurality of exciting light sources arranged along circumference at a predetermined central angle, the light source selecting part selects one from the plural light sources provided in the exciting light source arrangement plate and allows passing of the light of the light source, while shielding light from other light sources, and the light emitting optical system is a box body through which the light from the light source can pass, where each bundle of the connecting ends of the plural light emitting optical fibers are arranged at a position to which the light from the corresponding exciting light source can be directly emitted.

The eleventh aspect of the invention is an optical fiber measurement method comprising: a holding step of holding a reaction solution containing a fluorescent substance in respective liquid holding portions provided in a planar liquid holder, each liquid holding portion being arranged along a flat face; a light emitting step of emitting excitation light concurrently from a plurality of measurement ends into each of the entire or part of the plural liquid holding portions of the planar liquid holder; a light receiving step of receiving fluorescence for each liquid holding portion from each of the plural liquid holding portions to which the excitation light is emitted, by using the measurement ends; and a converting step of conducting photoelectric conversion while sequentially introducing the fluorescence that is sequentially selected one by one from the fluorescence received for each of the liquid holding portions and has a wavelength or a wavelength band sequentially selected one by one from plural kinds of wavelength or wavelength bands, into one photoelectric element.

The "measurement end" has a bundle of one light emitting end of the light emitting optical fiber emitting the excitation light, and one light receiving end of the light receiving optical fiber receiving light generated in the liquid holding portion. The plural measurement ends, supported by a measurement head, may be positioned at respective liquid holding portions. It is sometimes the case that the holding step is followed by a temperature control step of controlling temperature in the liquid holding portion.

The twelfth aspect of the invention is an optical fiber measurement method, wherein in the converting step, connecting ends on the opposite side of the light receiving ends of the light receiving optical fibers that are arranged and supported plurally at a predetermined central angle along a circumference on a connecting end arrangement plate, and plural kinds of optical filters arranged at a predetermined central angle along a circumference that has a same diameter and concentric with the circumference in the connecting end arrangement plate, on a light receiving rotary plate provided oppositely, closely to the connecting end arrangement plate and provided to be rotatable concentrically with the circumference of the connecting end arrangement plate, are optically connected sequentially one by one by rotation of the light receiving rotary plate and stopping for a predetermined connecting time, whereby the light having passed both of these is independently allowed to enter a central axis region of the light receiving rotary plate, and sequentially introduced into the photoelectric element and converted.

The thirteenth aspect of the invention is an optical fiber measurement method, wherein in the converting step, during rotation of a total of 360 degrees by repetition of rotation in a constant direction by an equivalent angle of the light receiving rotary plate and stopping for a predetermined connecting time, every combination of all of the connecting ends provided in the connecting end arrangement plate and all of the optical filters provided in the light receiving rotary plate is optically connected one by one, and the light having passed both of these is guided to the photoelectric element.

The fourteenth aspect of the invention is an optical fiber measurement method, wherein in the converting step, connecting ends on the opposite side of the light receiving ends of the light receiving optical fibers that are arranged and supported plurally at a predetermined central angle along a circumference on a connecting end arrangement plate, and plural optical filters provided on an optical filter arrangement plate having the optical filters provided movably with respect to a rotation axial line of a light guiding rotary plate for light reception selection that is provided oppositely to the connecting end arrangement plate and provided to be rotatable concentrically with the circumference of the connecting end arrangement plate, for guiding the light entered from the connecting ends to outgo approximately along its rotation axial line, are optically connected sequentially one by one by rotation of the light guiding rotary plate, movement of the optical filter arrangement plate and stopping for a predetermined connecting time, so that the light outgoing from the light guiding rotary plate can sequentially enter, and the light having passed both of these is sequentially introduced into the photoelectric element and converted.

The fifteenth aspect of the invention is an optical fiber measurement method, wherein in the converting step, during rotation of a total of 360 degrees by repetition of rotation in a constant direction of the light guiding rotary plate and a predetermined connecting time, the optical filters are optically connected sequentially, and the light having passed both of these is guided to the photoelectric element.

Advantageous Effects of Invention

According to the first aspect or the eleventh aspect of the invention, it is possible to emit and receive fluorescence from plural liquid holding portions concurrently by using a plurality of light receiving optical fibers and light emitting optical fibers, and by sequentially selecting and guiding light of a predetermined wavelength or wavelength band of respective received fluorescence to the photoelectric element, it is possible to sequentially conduct photoelectric conversion on fluorescence of plural wavelengths or wavelength band from plural liquid holding portions using one photoelectric element, so that even when measurement is conducted using a number of liquid holding portions and by labeling with various fluorescence, the process can be conducted rapidly while the production cost and measurement cost are reduced and expansion of the device scale is prevented. Further, by combining with a dispensing device, highly efficient and highly reliable automation from dispensing to measuring can be provided.

According to the second aspect or the twelfth aspect of the invention, since a predetermined wavelength or wavelength band of fluorescence from the light receiving optical fiber can be sequentially selected through the optical filter and sequentially guided to the photoelectric element by rotating the rotary plate, it is possible to securely conduct the photoelectric conversion using one photoelectric element by a simple mechanism and operation even when measurement is conducted using a number of liquid holding portions and by labeling with various fluorescence.

According to the second aspect of the invention, since the light passing each optical filter can be independently guided to the photoelectric element by providing the light receiving rotary plate with a mirror or a prism, a simple and reliable process can be executed.

According to the third aspect or the thirteenth aspect of the invention, since the light from every connecting end can pass through every optical filter by rotating the rotary plate by 360 degrees by repeating rotation of an equivalent angle and stopping for a predetermined connecting time, rapid and efficient control can be executed.

According to the fourth aspect or the fourteenth aspect of the present invention, although it is necessary to provide both the light guiding rotary plate and the optical filter arrangement plate to be independently movable, light from the light receiving optical fiber can be directly guided approximately along the rotation axial line, so that it is possible to measure in a clear condition while keeping the light intensity of the received light by avoiding interposition of a focusing lens and reducing the number of components of the optical system. Also, the light guiding rotary plate has a simple structure, and is easy to be produced.

According to the fifth aspect or the fifteenth aspect of the invention, since the light from every connecting end can pass through every optical filter by rotating the rotary plate by 360 degrees by repeating rotation in a constant direction, movement and stopping for a predetermined connecting time, rapid and efficient control can be executed.

According to the sixth aspect of the invention, by providing a measurement end having a light receiving end and a light emitting end relatively movable with respect to the planar container, there is no need to provide the measurement end for every liquid holding portion, and structure of the light reception selecting element or the like can be simplified, and the device scale can be reduced.

According to the seventh aspect of the invention, since plural kinds of excitation lights can be readily selected and emitted by using the light source selecting element, measurement can be conducted for a variety of objects using various fluorescence.

According to the eighth aspect of the invention, since plural kinds of light sources themselves are selected, and plural kinds of optical filters can be selected and combined, it is possible to emit excitation light of various wavelengths to the liquid holding portion, and detailed process can be executed, and diversity is realized.

According to the ninth aspect of the invention, since selection of light source and light guidance can be conducted using the light guiding rotary plate, it is possible to contract and simplify the device scale. Further, since light of the light source is guided to a bundle of connecting ends of light emitting optical fibers, light can be emitted on each of the plural liquid holding portions efficiently.

According to the tenth aspect of the invention, since light of the light source is guided to the bundle of connecting ends of light emitting optical fibers by allowing transmission of light in the box body, it is possible to emit light to each liquid holding portion with a simple structure, and to reduce the number of components, leading reduction in production cost.

BRIEF DESCRIPTION OF DRAWINGS

FIG. 4 is a table showing operation conditions of the components shown in FIG. 3.

DESCRIPTION OF EMBODIMENTS

Next, an optical fiber measurement device 10 according to a first embodiment of the present invention will be described based on drawings.

Figure 1:
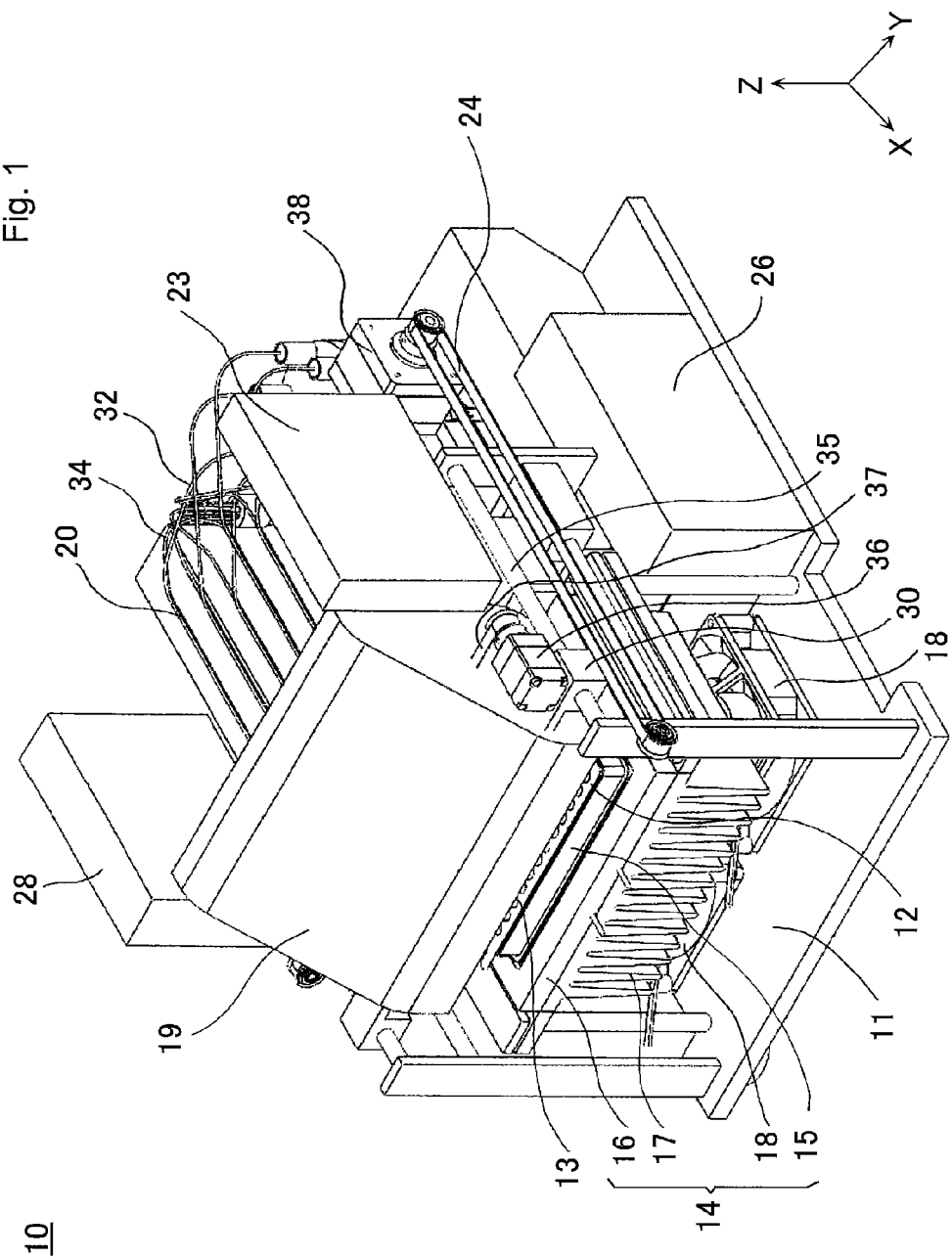
FIG. 1 is an overall perspective view of an optical fiber measurement device according to a first embodiment of the present invention.

FIG. 1 is an overall perspective view of an optical fiber measurement device 10 according to an embodiment of the present invention, and the device 10 is assembled on a substrate 11. The device 10 has a micro plate 12 serving as the planar liquid holder in which a plurality of (12×8=96, in this example) wells 13 serving as liquid holding portions capable of holding a PCR reaction solution containing a fluorescent substance are arranged along a flat face, and temperature control according to a PCR method is executed for each well 13. In FIG. 1, the micro plate 12 is almost hidden by a cover 19, and halves of twelve wells 13 in one line (along the Y axis) are barely visible. Here, a capacity of the well 13 is, for example, about 200 μL, and a liquid amount held therein is such that a predetermined given liquid amount is held in each well, and the level of liquid held in each well is at the same predetermined level. In the case of PCR, it is, for example, about 50 μL.

Under the micro plate 12, a temperature controller 14 for executing temperature control of each of the wells 13 provided in the micro plate 12 is provided, and the temperature controller 14 has a block 15 provided with a hole fitting with each well 13 of the micro plate 12, a heating and cooling part 16 provided under the block 15, in which a Peltier device is disposed in a heat insulating material, a fin 17 provided under the heating and cooling part 16, and a fan 18 provided under the fin 17.

The upper side of the micro plate 12 is covered with a transparent film 21 serving as the thin film, so that the openings of ninety-six wells 13 of the micro plate 12 are blocked up and evaporation of the liquid, entry of foreign substances from outside, and cross contamination are prevented.

The device 10 has a guide member 30 guiding the measurement head (40, see FIG. 2) in the anteroposterior direction (X-axis direction) along a guide rail 35 of the device 10, and a timing belt 24 and an X-axis driving motor 38 which are an X-axis shifting mechanism for shifting the guide member 30 and the measurement head (40, see FIG. 2) coupled therewith in the anteroposterior direction. Here in the measurement head (40), bundle ends 22a to 22f of respective tip ends of a plurality (six sets in this example) of optical fiber bundles 20a to 20f made up of light receiving optical fibers 32a to 32f and light emitting optical fibers 34a to 34f are arranged at such intervals (18 mm pitch in this example) that they are at respective predetermined height positions above plural wells among twelve wells 13 in one line of the micro plate 12, for example above six wells 13 arranged every other well. The bundle ends 22a to 22f of the optical fiber bundles 20a to 20f are provided in such a manner that light-receiving ends at the tip ends of the light receiving optical fibers 32a to 32f and light emitting ends at the tip ends of the light emitting optical fibers 34a to 34f are bundled.

The device 10 further has timing belt 37 and Y-axis driving motor 36 which are a Y-axis shifting mechanism for shifting the measurement head (40, see FIG. 2) by one pitch of the well 13 in both the forward and reverse directions along a width direction (Y-axis direction).

Here, the reference numeral 23 denotes a board for motor control, the reference numeral 26 denotes a power supply module, and the reference numeral 28 denotes, for example, a control board incorporating a CPU for controlling various controls including temperature control.

Figure 2:
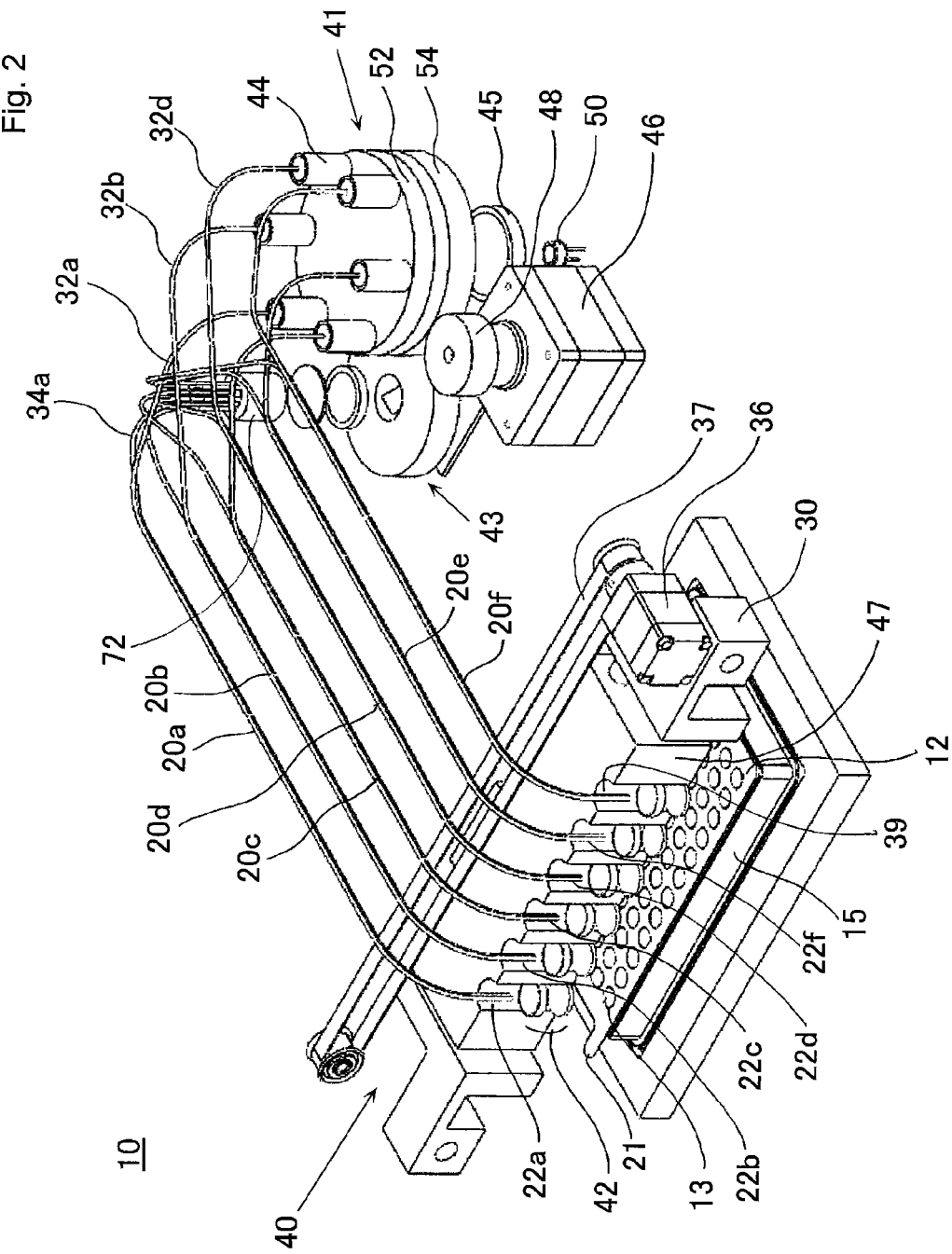
FIG. 2 is a partially cutaway perspective view of primary components of the device shown in FIG. 1.

FIG. 2 is an enlarged partially cutaway view of primary part of the device 10 shown in FIG. 1, namely, the measurement head 40 hidden by the cover 19, and a light reception selecting element 41 (and a photoelectric element 50) connected thereto via the light receiving optical fibers 32a to 32f and the light emitting optical fibers 34a to 34f of the optical fiber bundles 20a to 20f, and an optical system connected with a light source selecting element 43 (and a light source for excitation light 80).

The measurement head 40 has a support member 47 provided with six supporting holes 39 (in the drawing, shown by being cut away into a semicircular cross section) pierced in line along the width direction (Y-axis direction) at a pitch that is twice the pitch between the wells 13 of the micro plate 12, the bundle ends 22a to 22f of six sets of the optical fiber bundles 20 bundling one light receiving end which is an end part of the light receiving optical fiber 32 and one light emitting end which is an end part of the light emitting optical fibers 34, provided for each of the supporting holes 39, and compound lenses 42 made up of a concave lens and a convex lens, provided below the bundle ends 22a to 22f. The bundle ends 22a to 22f and the compound lenses 42 get together to correspond to six measurement ends 25a (22a, 42) to 25f (22f, 42). Diameters of these light receiving optical fiber 32 and light emitting optical fiber 34 are for example, 0.5 mm, and the compound lens 42 is arranged, for example, for making the one traveling in the Z-axis direction among fluorescence generated in the well 13 enter parallel with the bundle ends 22a to 22f of the measurement ends 25a to 25f in such a manner that the diameter of the beam of the received fluorescence is narrowed, and for making excitation light from the light emitting optical fiber 34 emit parallel with the opening by extending the diameter of the beam. The lens diameter of the compound lens 42 is not less than 9 mm, and 10 mm in this example so that fluorescence radiated in the vertical direction from each well 13 can sufficiently enter, in the case of a liquid holder where the wells 13 are arranged in a pitch of 9 mm.

The support member 47 is movable in the X-axis direction while it is coupled with the guide member 30, and is also movable by one pitch between the wells 13 in the Y-axis direction while it is coupled with the timing belt 37 which is the Y-axis shifting mechanism. By movement of one pitch of the well 13 in the Y-axis direction, it is possible to make the compound lenses 42 be positioned above twelve wells 13 arranged in line of the micro plate 12. The Z-axis direction is kept at a constant height position from the micro plate 12 serving as the planar liquid holder.

Among six sets of the optical fiber bundles 20a to 20f, six light receiving optical fibers 32a to 32f are connected, at connecting ends on the opposite side of the light receiving ends, with the light reception selecting element 41 via six connectors 44, and six light emitting optical fibers 34a to 34f are connected, at connecting ends on the opposite side of the light emitting ends, with a light guiding rotary plate for light source selection 66 of the light source selecting element 43 and so on, respectively via a connector 72. The reference numeral 45 denotes lens system 45 that is provided to have a lens surface in the center axial region, and to introduce the light entering the lens system 45 at a predetermined incidence angle into the photoelectric element 50. The reference numeral 46 denotes a motor for a rotating light receiving rotary plate 54 as will be described later, of the light reception selecting element 41, and the reference numeral 48 denotes a roller rotationally driven by the motor 46, for rotationally driving the light receiving rotary plate 54 while contacting with the outer circumference of the light receiving rotary plate 54.

Figure 3:
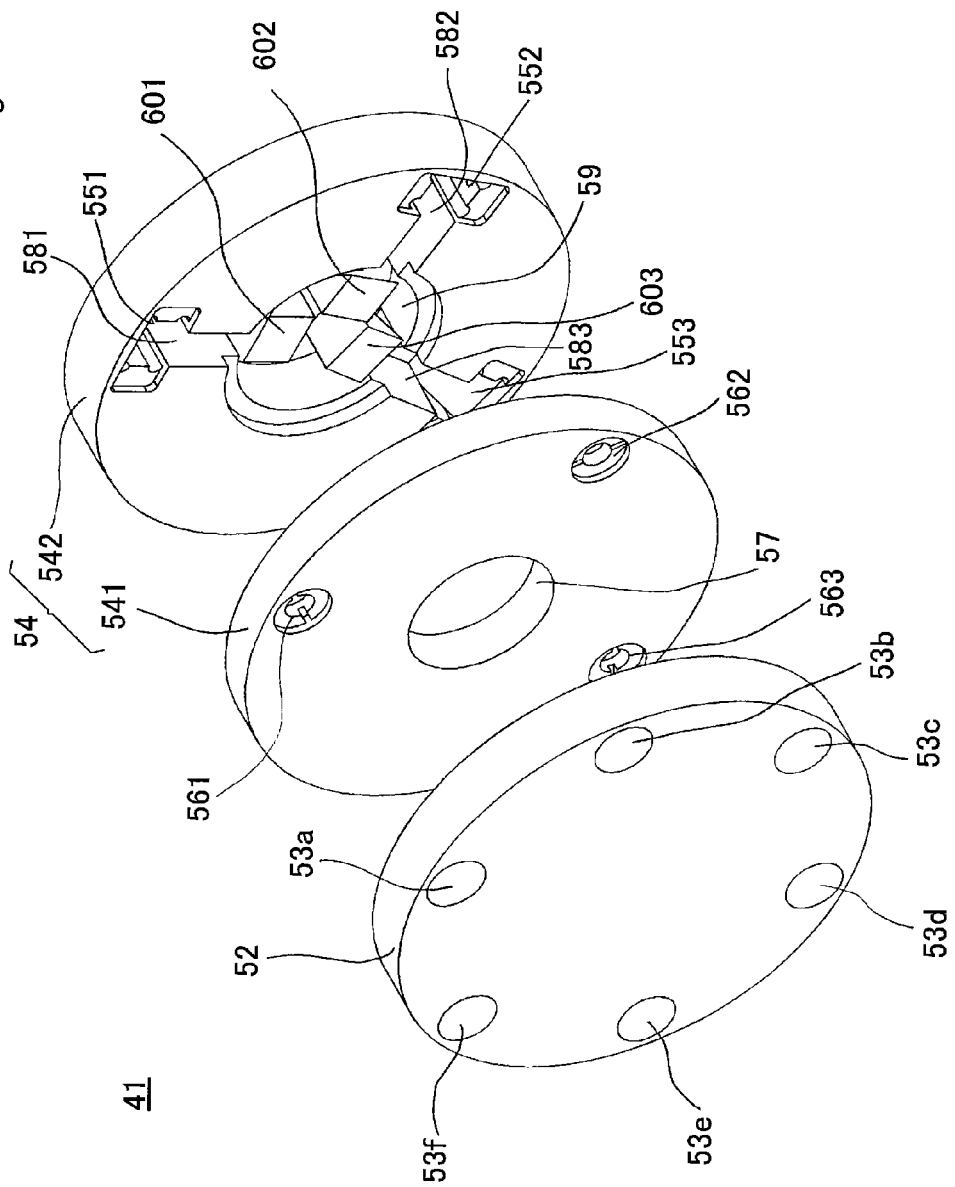
FIG. 3 is a partially enlarged exploded perspective view of the primary components shown in FIG. 2.

FIG. 3 is a perspective view showing the light reception selecting element 41 in an exploded manner.

The light reception selecting element 41 has fixed the connecting end arrangement plate 52 in the shape of a disc of about 7 cm in diameter, and supporting plural (six, in this example) connecting ends 53a to 53f on the opposite side of the light receiving ends, among the bundle ends 22a to 22f of the light receiving optical fibers 32a to 32f, arranged along the circumference (for example, about 6 cm in diameter) via the connectors 72 in such a manner that the central angle between neighboring connecting ends 53a to 53f with respect to the center of the circumference has the same angle (60 degrees in this example) that is obtained by dividing equally into the plural numbers (six, in this example), and the light receiving rotary plate 54 that is provided oppositely, closely to the connecting end arrangement plate 52, and concentrically with the circumference of the connecting end arrangement plate 52, and formed, for example to have the same diameter (diameter about 7 cm) and is rotatable with respect to the connecting end arrangement plate 52.

The light receiving rotary plate 54 has optical filter arrangement plate 541 provided with a plurality of (three, in this example) optical filters 56 (561, 562, 563) arranged along a circumference that is concentric with the circumference along which the connecting ends 53a to 53f of the connecting end arrangement plate 52 are arranged and has the same diameter therewith (for example, diameter about 6 cm), and an optical system arrangement plate 542 connected with the optical filter arrangement plate 541 and provided with a plurality of (three, in this example) light receiving optical systems (551, 601) to (553, 603) having the same structure, that are connected with the optical filters 561 to 563 one-on-one, capable of guiding the light having passed through each of the optical filters 561 to 563 independently to the central axis region where the central axis (coincidence with rotation axial line) of the light receiving rotary plate 54 penetrates. The reference numeral 57 denotes a circular hole in the center.

Therefore, the three optical filters 561 to 563 and the three light receiving optical systems (551, 601) to (553, 603) have the same central angle with respect to the center of said circumference. It can be said that one of these neighboring central angles, or neighboring plural central angles summing up neighboring central angles should not have a central angle (each 60 degrees in this example) formed by neighboring the connecting ends 53a to 53f arranged as described above or a central angle of natural number times of such a central angle formed by neighboring ones. This is because when the light receiving rotary plate 54 has such a central angle, two or more optical filters and connecting ends are concurrently connected, and lights from two or more light receiving optical fibers 32 are concurrently guided to the central axis region of the light receiving rotary plate 54, so that "guiding the light having passed through each of the optical filters independently to the central axis region of the light receiving rotary plate" is not satisfied.

Here, as the light receiving optical systems (551, 601) to (553, 603), the optical filters 561 to 563 are provided in such a manner that they are embedded in a hole pierced in the optical filter arrangement plate 541, and the light receiving optical systems (551, 601) to (553, 603) are provided in such a manner that they are embedded in circular hole 59 pierced in the center of the optical system arrangement plate 542 and in three grooves 581 to 583 extending radially in the radial direction from the circular hole 59. These grooves 581 to 583 will be blocked by being coupled with the optical filter arrangement plate 541.

The light receiving optical systems (551, 601) to (553, 603) have outer mirrors 551 to 553 provided in the respective grooves 581 to 583 near the outer circumference of the optical system arrangement plate 542 that reflects the light passing through the optical filters 561 to 563 of the optical system arrangement plate 542 in the normal direction, and three inner mirrors 601 to 603 provided inside the circular hole 59 for reflecting the light reflecting at the outer mirrors 551 to 553 and traveling through each groove 581 to 583 and making it enter the lens surface of the lens system 45 in the central axis region through the hole 59. Therefore, the light having passed the optical filters 561 to 563 travels inside the light receiving rotary plate 54, so that it will not be disturbed by stray light from outside. Here, the lens system 45 is provided on the outer side of the light receiving rotary plate 54 on the side where the optical filter arrangement plate 541 is not provided so that its central axis coincides with its optical axis.

FIG. 4 is a table showing combinations of the light receiving optical fibers 32a to 32f and filters 561 to 563 by which when the neighboring central angles of three sets of the optical filters 561 to 563 and light receiving optical systems (551, 601) to (553, 603) are set at 100 degrees, 100 degrees and 160 degrees, the fluorescence generated at the time when the light receiving rotary plate 54 is rotated sequentially by 20 degrees in one direction (No. 2 to No. 18) from the condition that connecting end 53a of the light receiving optical fiber 32a is connected with the optical filter 561 (No. 1), is guided to the photoelectric element 50.

According to the table, while the light receiving rotary plate 54 is rotated one revolution intermittently in one direction by a certain angle (here by 20 degrees), either one of the light receiving optical fibers 32a to 32f is sequentially selected and connected with either one of the fibers, and the fluorescence from the light receiving optical fibers is allowed to pass sequentially to sequentially deliver to the photoelectric element 50, so that it is possible to conduct the switching operation simply and quickly.

Figure 5:
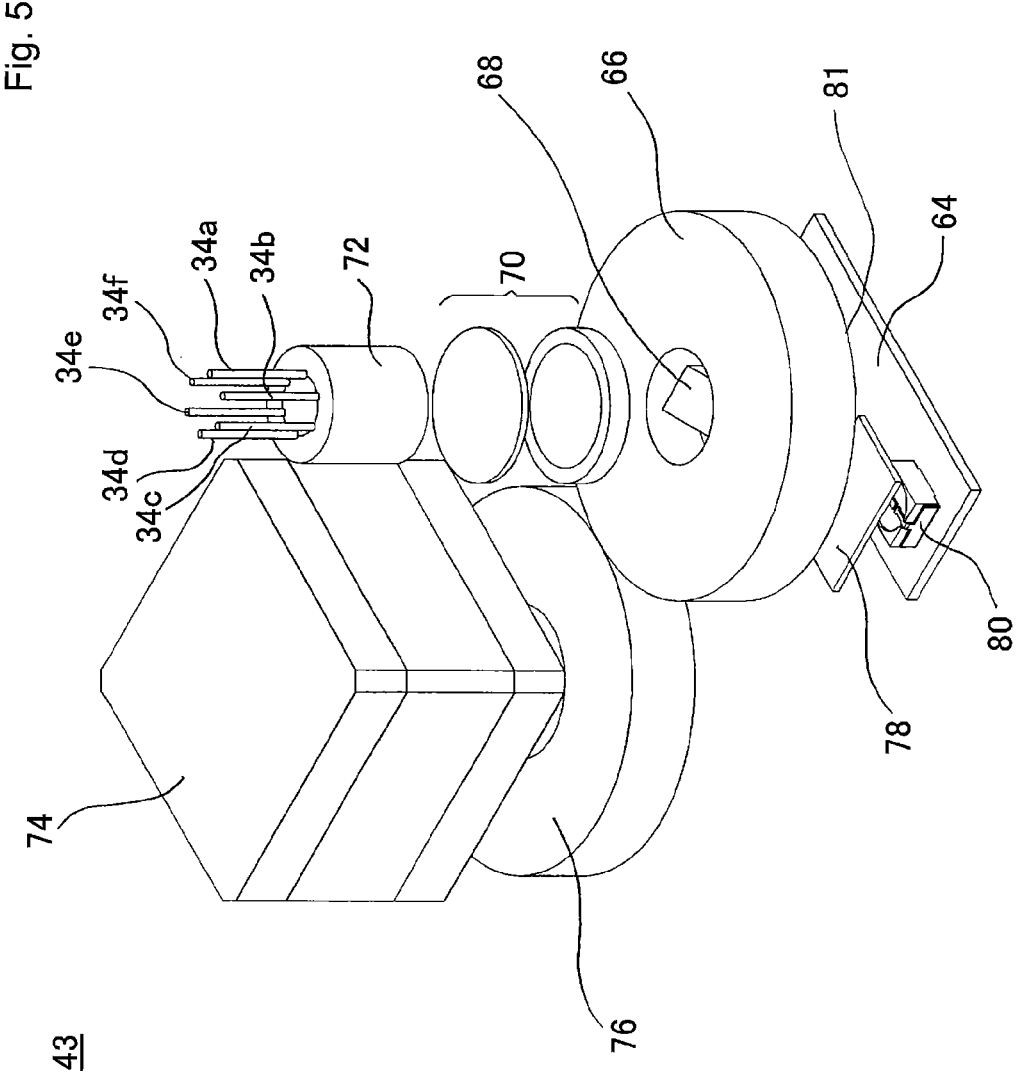
FIG. 5 is a partially enlarged exploded perspective view of the primary components shown in FIG. 2.

FIG. 5 is an enlarged view of the light source selecting element 43. The light source selecting element 43 has power LEDs 80, 81 as two kinds of light sources provided fixedly to a fixing plate 64 at an interval, two kinds of filters 78 that allow transmission of a predetermined wavelength for the power LEDs 80, 81, the light guiding rotary plate for the light source selection 66 that is provided to make the light having transmitted the filter 78 travel along the radial direction by an inner mirror 68 and an outer mirror 69 (see FIG. 6) to eventually travel along the central axis region (where lens surface of the lens system 45 is provided) direction in order to select either of the power LEDs 80, 81 (see FIG. 6) and provided in a rotatable manner so that the rotation axial line coincides with the central axis, a compound lens 70 made up of combination of a convex lens and a concave lens, provided along the central axis of the light guiding rotary plate for the light source selection 66, and the connector 72 supporting a plurality of (six, in this example) the light emitting optical fibers 34a to 34f arranged circularly along the central axis direction.

The light guiding rotary plate for light source selection 66 is rotationally driven by a rotor 76 through contact between its outer circumference and the rotor 76 that is rotationally driven by a motor 74. By rotating the light guiding rotary plate for light source selection 66 by 180 degrees, it is possible to switch between the power LEDs 80, 81 as a light source.

Figure 6:
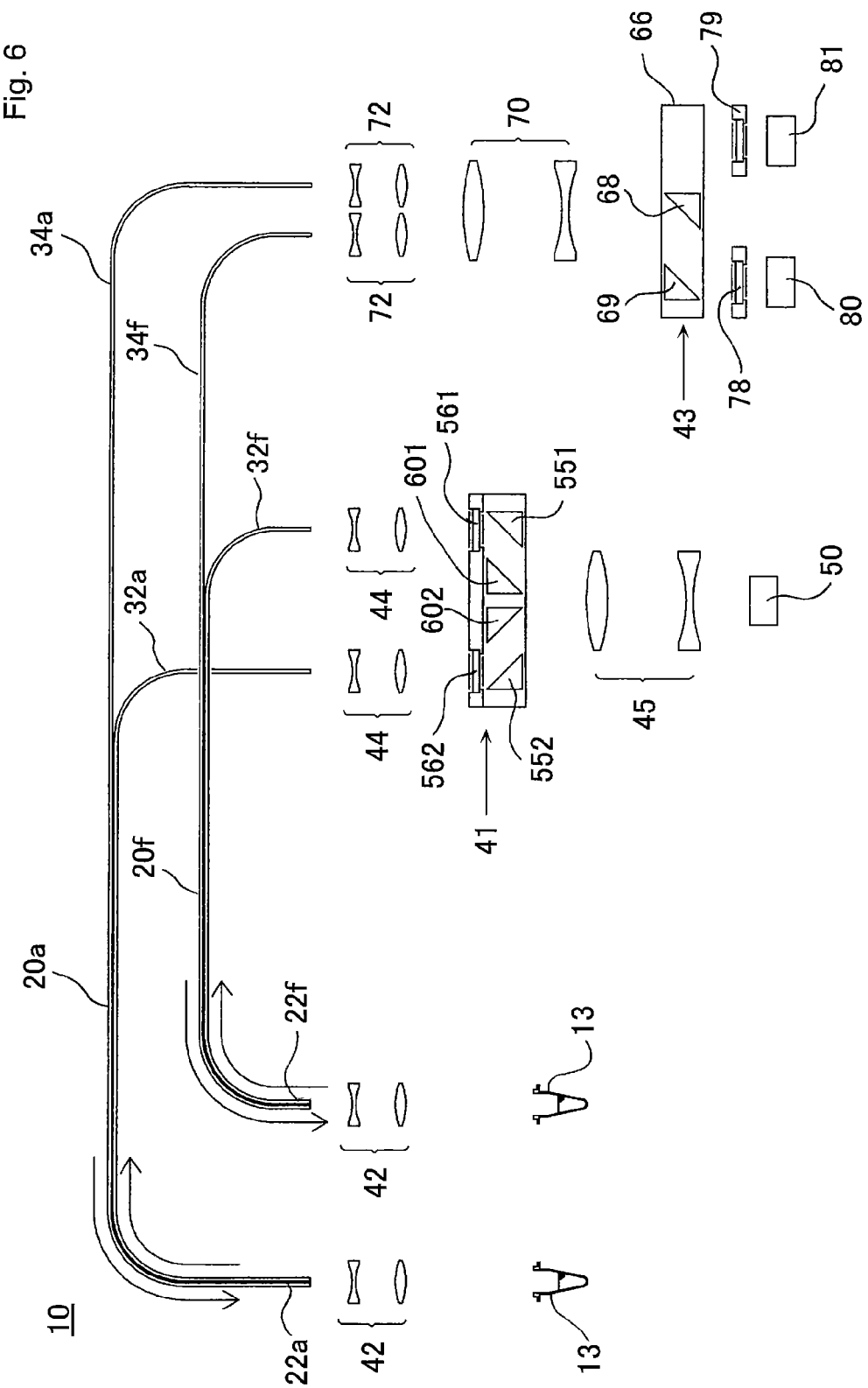
FIG. 6 is an overall schematic view of the optical fiber measurement device according to the first embodiment of the present invention.

FIG. 6 is a system diagram showing the connection state of the entire optical system of the device 10 according to the present embodiment. According to this diagram, each of the connectors 44, 72 is provided therein with a compound lens made up of a concave lens and a convex lens, and each compound lens is provided so as to make the light output from the light receiving optical fibers 32a to 32f enter the light reception selecting element 41 as light perpendicular to the filter surface, or to make the light from power LEDs 80, 81 enter along the axial direction of the light emitting optical fibers 34a to 34f.

Figure 7:
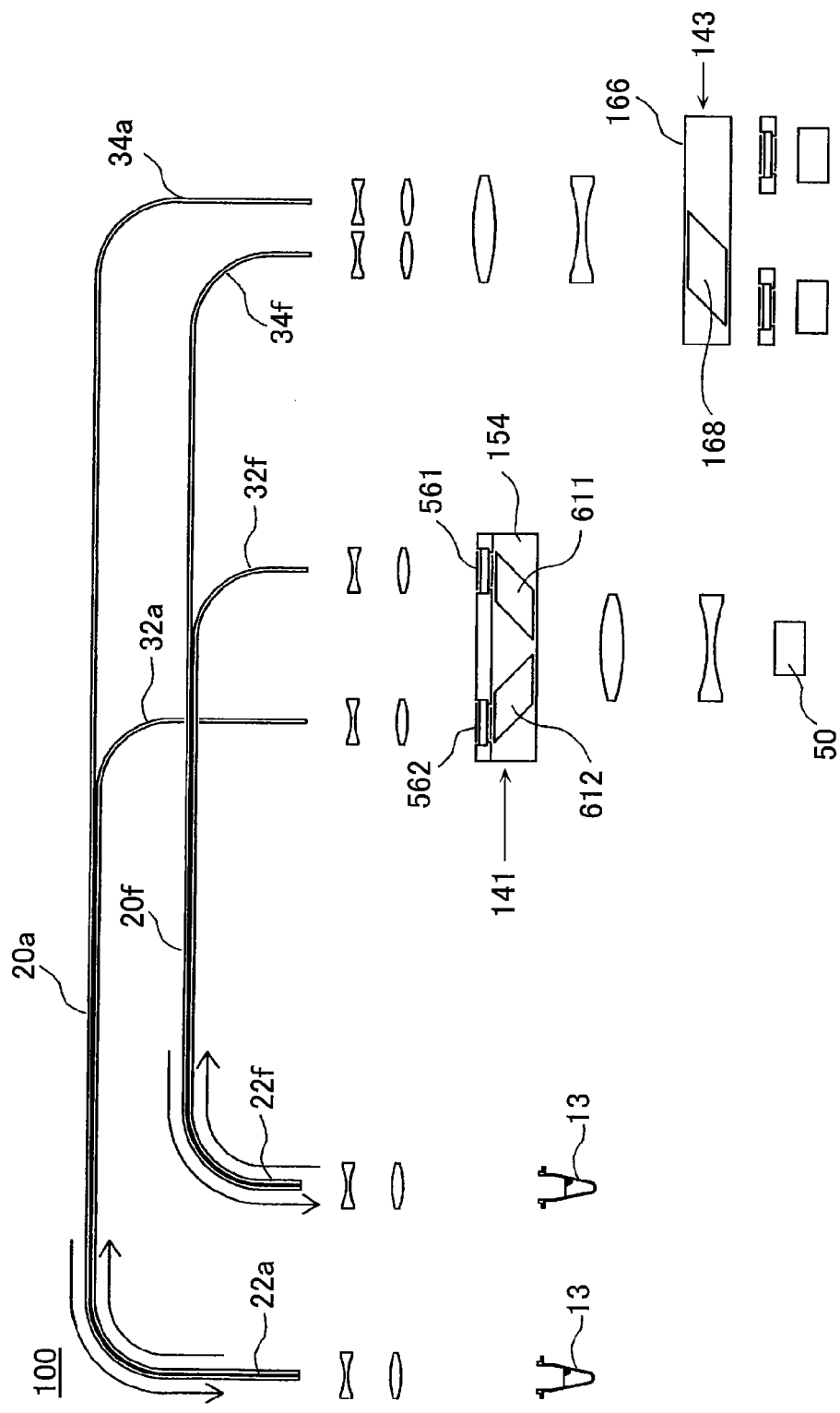
FIG. 7 is an overall schematic view of an optical fiber measurement device according to a second embodiment of the present invention.

FIG. 7 is a system diagram showing the connection state of the entire optical system of a device 100 according to other embodiment. In this embodiment, a light reception selecting element 141 where three light receiving optical systems 611, 612 using a prism is used in place of three light receiving optical systems (551, 601) to (553, 603) using a mirror, in light receiving rotary plate 154, and a light source selecting element 143 where prism 168 is used in place of the light source selecting element 43 using a mirror in rotary plate for light source selection 161 are shown. For the one identical to that in FIG. 6, the reference numeral and description thereof will not be repeated. In this case, the prism is arranged while it is embedded in the hole and grooves provided in the light receiving rotary plate 154.

Next, an operation of an optical fiber measurement device 10 according to an embodiment of the present invention will be described. A micro plate 12 where ninety-six wells 13 holding a PCR reaction solution containing a fluorescent substance applied by a dispenser in advance are arranged along a flat face is covered with a film 21, and loaded in the optical fiber measurement device 10.

For the loaded the micro plate 12, temperature control according to the PCR method is started by a temperature controller 14 provided under the same. Simultaneously, the measurement head 40 is shifted in the X-axis direction using a timing belt 24 and an X-axis driving motor 38 which are the X-axis shifting mechanism, to position bundle ends 22a to 22f of the six optical fiber bundles 20a to 20f provided in the measurement head 40 and six measurement ends 25a to 25f formed of a compound lens 42 on the first line of the micro plate 12, and using the timing belt 37 and a Y-axis driving motor 36, the measurement ends 25a to 25f of the optical fiber bundles 20a to 20f are positioned closely above the film 21 of six wells 13 at every other line along the column direction of the wells 13 of the first line, and through the film 21, and through the light emitting optical fibers 34a to 34f of the optical fiber bundles 20a to 20f, the light from the power LED 80 as a light source that is output after a transmitting filter 78 is selected by the light guiding rotary plate for light source selection 66 and a beam of excitation light is emitted inside the well 13 through the film 21 via the compound lens 42. Fluorescence outgoing from the well 13 in response to the emission of the excitation light is received by the measurement end and transmitted thorough the light receiving optical fibers 32a to 32f of the optical fiber bundles 20a to 20f, and input into the photoelectric element 50 by the light reception selecting element 41 through the predetermined filters 561 to 563.

At this time, when the light receiving rotary plate 54 is in the condition of No. 1 of the table of FIG. 4, the light from the light receiving optical fibers 32a is received through the filter 561 and input into the photoelectric element 50, and intensity of the light is converted into an electric signal and transmitted to an optical analyzer consisting of an information processing device including CPU or the like. Then, by rotating to the condition of No. 2 in the table of FIG. 4 where the light receiving rotary plate 54 is rotated by 20 degrees at a constant rotation speed (for example, 50 milliseconds), for example, after 50 milliseconds from stopping at the position of No. 1, the light from a light receiving optical fiber 32c is received via the filter 562 and input into the photoelectric element 50, and intensity of the light is converted into an electric signal and transmitted to the optical analyzer. Similarly, for example, by sequentially rotating by 20 degrees every 50 milliseconds from No. 3 to No. 18 in the table of FIG. 4, it is possible to obtain the light passed through three kinds of filters 561 to 563 for every light receiving optical fiber 32a to 32f in a total of 1.8 seconds per one revolution.

Next, by rotating the light guiding rotary plate for the light source selection 66 by 180 degrees, the light from the power LED 81 as a light source is selected and excitation light is emitted inside the well 13 through the film 21. Fluorescence outgoing from the well 13 in response to the emission of the excitation light is received by the light receiving optical fibers 32a to 32f of the optical fiber bundles 20a to 20f, and received thorough the predetermined filters 561 to 563 inside the light reception selecting element 41 and input into the photoelectric element 50. At this time, as described above, by sequentially rotating the light receiving rotary plate 54 according to FIG. 4, it is possible to obtain the light passed through three kinds of the filters 561 to 563 for every light receiving optical fiber 32a to 32f in a total of 3.6 seconds. Therefore, for the process regarding the six wells 13, the process is completed in about 4 seconds.

As the next step, by shifting the measurement ends 25a to 25f of each of the six fiber bundles 20a to 20f of the measurement head 40 by one pitch in the Y-axis direction by means of the timing belt 37 which is a Y-axis mechanism, other six wells 13 at every other line in the first line of the micro plate 12 are positioned closely above the film 21, and the process as described above is repeated. Therefore, the process of the first line completes in about 8 seconds.

Next, by shifting the measurement head 40 by one line along the X-axis direction using the timing belt 24 and the X-axis driving motor 38 serving as the X-axis shifting mechanism, it can be positioned on the second line of the micro plate 12. For each well 13 on the second line, a sequential measurement process is conducted in a similar manner as described above, and a similar measurement process is conducted for every well 13 in the second line in 8 seconds.

Similarly, the process is conducted for every eight lines, and in this example, the operation takes a total of about 64 seconds excluding the shifting time of X axis and Y axis.

Figure 8:
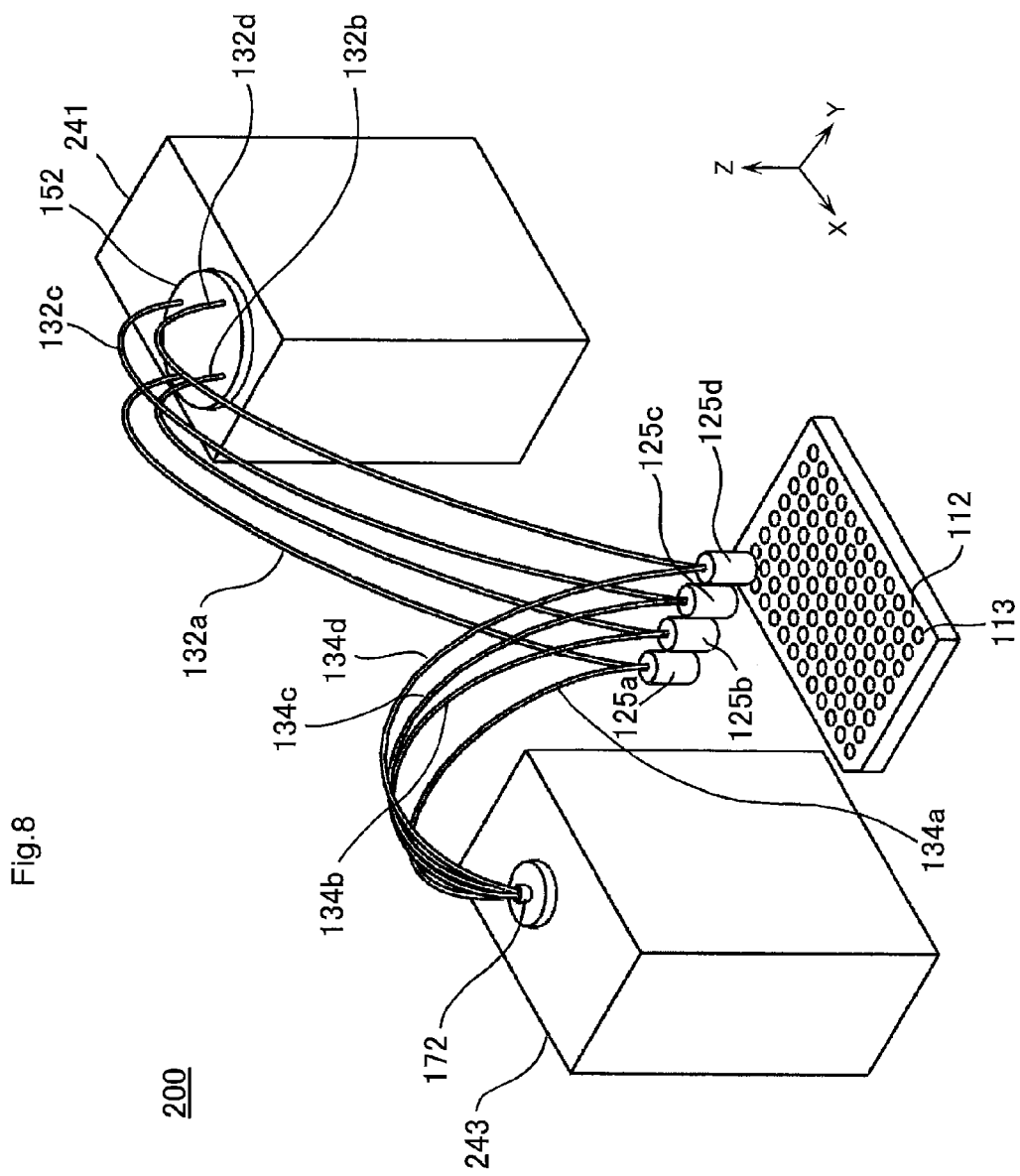
FIG. 8 is a perspective view showing a primary part of an optical fiber measurement device according to a third embodiment of the present invention.
Figure 9:
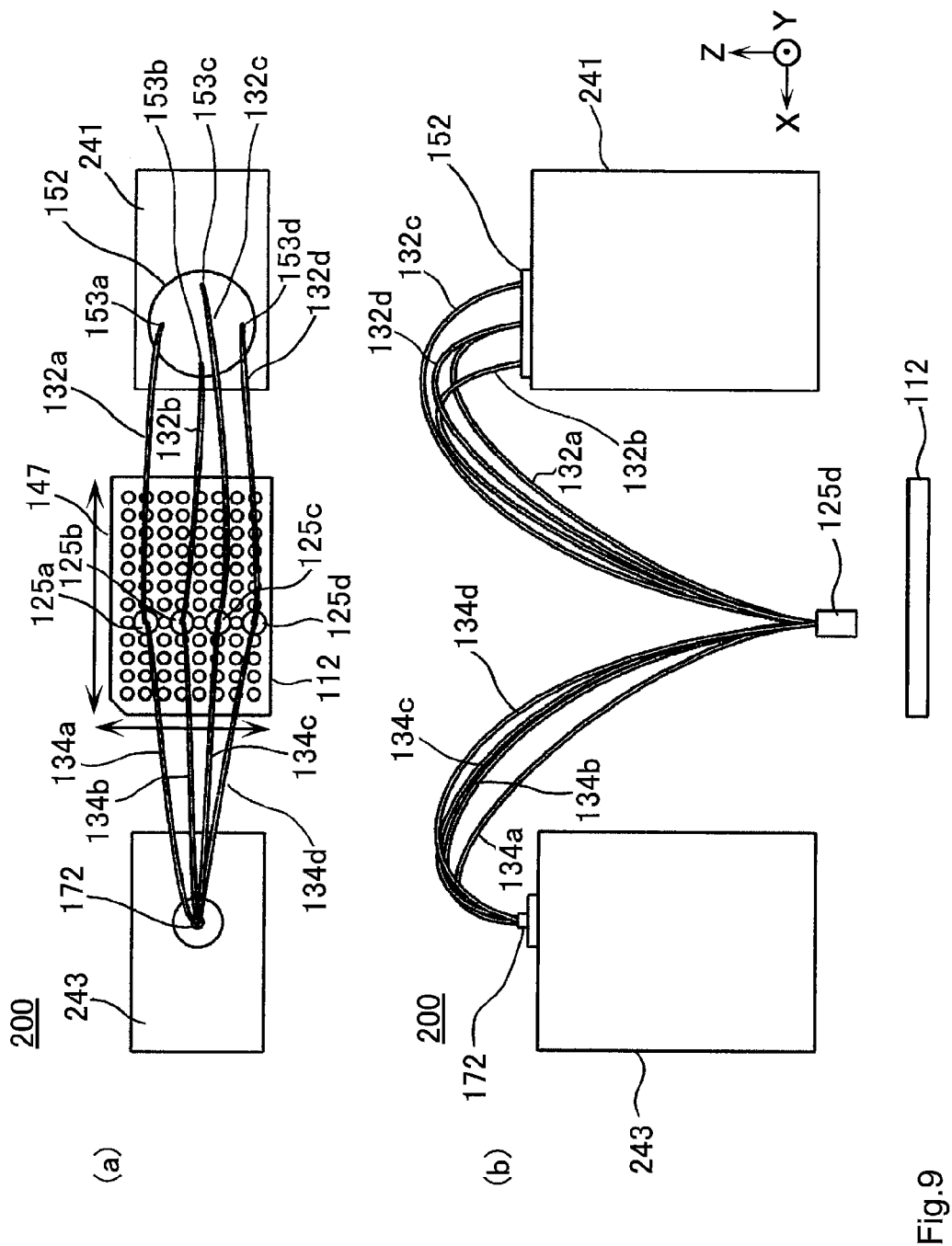
FIG. 9 is a plan view and a front view of the primary part shown in FIG. 8.

FIGS. 8 and 9 show a primary part of an optical fiber measurement device 200 according to a third embodiment of the present invention. The device 200 has a micro plate 112 serving as a planar liquid holder in which a plurality of (8×12=96, in this example) wells 113 as liquid holding portions capable of holding a PCR reaction solution containing a fluorescent substance are arranged along a flat face. In this example, eight wells 113 are arranged along the Y-axis direction and twelve wells 113 are arranged along the X-axis direction.

On the micro plate 112, as the one corresponding to the measurement head, four measurement ends 125a, 125b, 125c, 125d are provided fixedly to the substrate of the device. These four measurement ends 125a to 125d are arranged at such an interval (18 mm pitch, in this example) that they are above plural wells 113, for example, four wells 113 arranged every other well among eight wells 113 of one line of the micro plate 112.

Each of the measurement ends 125a to 125d is optically connected with respective one pair of a light receiving end which is one end of each light receiving optical fiber 132a to 132d and a light emitting end which is one end of each light emitting optical fiber 134a to 134d, and a connecting end which is the other end of the each light receiving optical fiber 132a to 132d is optically connected with a light reception selecting unit 241 corresponding to a light reception selecting element, and a connecting end which is the other end of each of the light emitting optical fibers 134a to 134d is optically connected with a light source selecting unit 243 (and a photoelectric unit 150 corresponding to a photoelectric element) corresponding to a light source selecting element.

The measurement head consists of four measurement ends 125a to 125b attached to a support member that is fixed to the substrate and provided with four supporting holes pierced in line along the width direction (Y-axis direction) at a pitch twice the pitch between the wells 113 of the micro plate 112. In the measurement ends 125a to 125d, under a tip end of a pair of each light receiving optical fiber 132a to 132d and each light emitting optical fiber 134a to 134d, a compound lens made up of a concave lens and a convex lens is provided. The function and the size of such a compound lens are as described in the first embodiment.

Since the measurement head is fixed, the micro plate 112 serving as a planar liquid holder is shifted unlike the case of the device 10 according to the first embodiment or a device 100 according to a second embodiment. In the present embodiment, when temperature control is not required, only the micro plate 112 is shifted. On the other hand, when the reaction requires temperature control as is the case of a PCR reaction, a temperature controller carrying out temperature control of the well 113 provided in the micro plate 112 is provided under the micro plate 112, and as described in an exemplary form of the first embodiment, the temperature controller has a heating and cooling part provided with a hole fitting with each well 113 of the micro plate 112, a fin provided under the heating and cooling part, and a fan provided under the fin, and the micro plate 112 is shifted together with these.

Unlike the device 10 according to the first embodiment and the device 100 according to the second embodiment, the optical fiber measurement device 200 according to the present embodiment has a mechanism for shifting the micro plate 112 in the X-axis direction and the Y-axis direction in place of the measurement head. The micro plate 112 is movable in the X-axis direction by the X-axis shifting mechanism implemented, for example, by a timing belt, and is also movable in the Y-axis direction by one pitch between the wells 113 while it is coupled with the Y-axis shifting mechanism implemented, for example, by a timing belt. As a result, it is possible to position the measurement ends 125*a* to 125*d* above eight wells 113 arranged in one line of the micro plate 112. The Z-axis direction is kept at a certain height position from the micro plate 112 serving as a planar liquid holder.

As to the four light receiving optical fibers 132*a* to 132*d*, a connecting end on the opposite side of the light receiving end is connected with a connecting end arrangement plate 152 of the light reception selecting unit 241, and as to the four light emitting optical fibers 134*a* to 134*d*, a connecting end on the opposite side of the light emitting end is connected with the connector 72 of the light source selecting unit 243.

Figure 10:
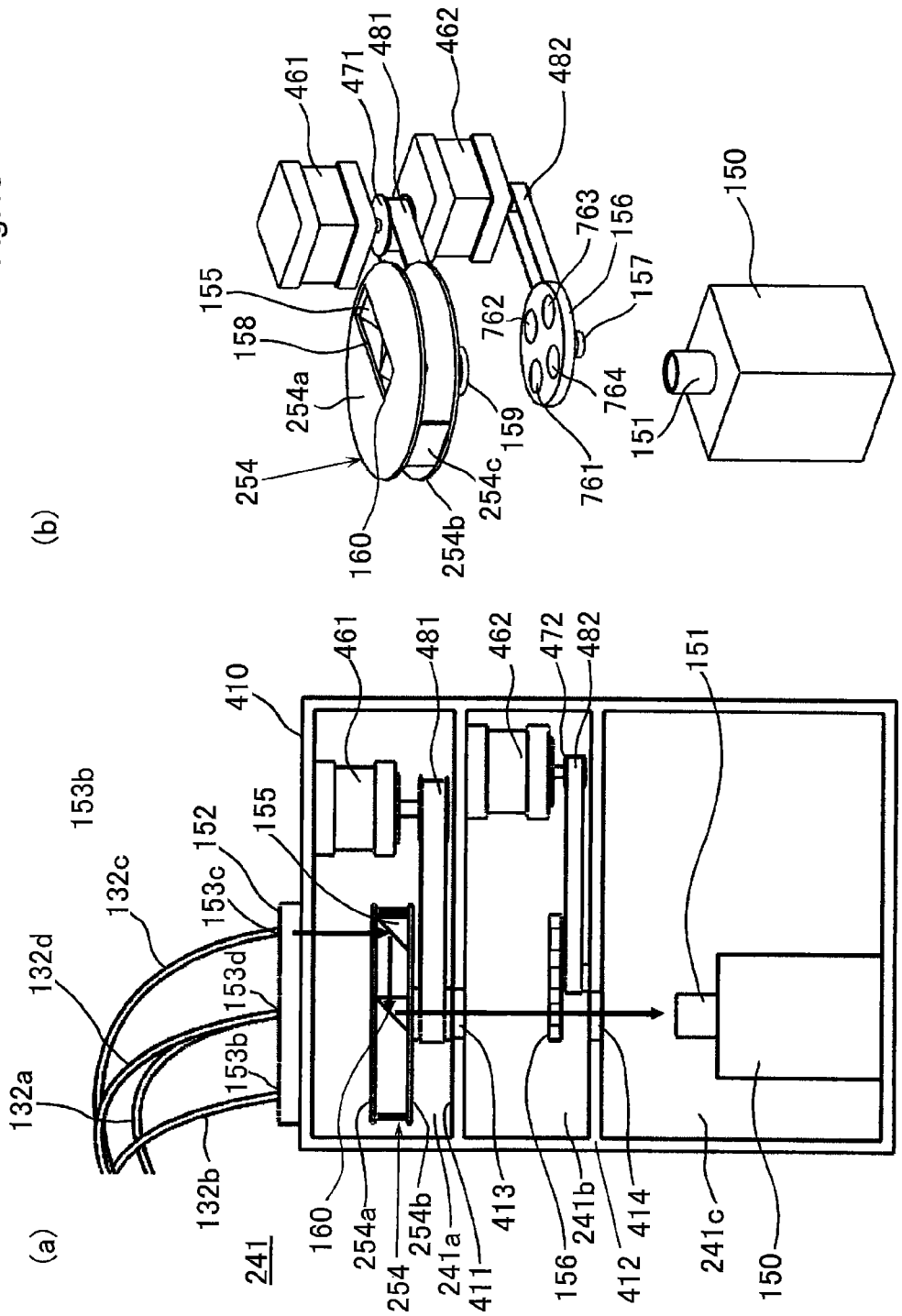
FIG. 10 is a partially cutaway lateral view and a partial perspective view of a light reception selecting unit of FIG. 8.

FIG. 10 is a view showing the light reception selecting unit 241.

As shown in FIG. 10(*a*), in the light reception selecting unit 241, an optical system is accommodated in a box body 410 partitioned into three dark rooms 241*a*, 241*b*, 241*c* by partition plates 411, 412. The top plate of the box body 410 is provided with, for example, the connecting end arrangement plate 152 in the shape of a disc of about 7 cm in diameter, supporting plural (four, in this example) connecting ends 153*a* to 153*d* on the opposite side of the light receiving end of the light receiving optical fibers 132*a* to 132*d*, along a circumference (for example, diameter 6 cm) as shown in FIG. 9 so that the central angle with respect to the center of the circumference between the neighboring connecting ends 153*a* to 153*c*, 153*c* to 153*d*, 153*d* to 153*b*, 153*b* to 153*a* has the equivalent angle (90 degrees in this example) obtained by equally dividing into the plural number (four, in this example).

As shown in FIG. 10(*a*), in the dark room 241*a*, light guiding rotary plate for light reception selection 254 is provided, and the light guiding rotary plate 254 is provided to be opposed to the connecting end arrangement plate 152 and is rotatable concentrically with the circumference of the connecting end arrangement plate 152, and guides the light entered from the connecting ends 153*a* to 153*d* sequentially and independently to outgo approximately along the rotation axial line.

As shown in FIGS. 10(*a*) and 10(*b*), the light guiding rotary plate 254 has two discs 254*a*, 254*b* and spacer 254*c* in the shape of a bent plate, and an optical system is provided in such a manner that it is sandwiched by the two discs 254*a*, 254*b* up and down. An upper disc 254*a* is pierced with a rectangular hole 158 along the radius of the disc 254*a*, and the center of a lower disc 254*b* is connected with a rotation axis 159 having a tubular shape pierced with a circular hole that is concentric with the rotation axial line, and the interior thereof can transmit the light approximately along the rotation axial line.

On the lower disc 254*b*, one reflecting prism 155 having a reflecting surface provided so that the light from each of the connecting ends 153*a* to 153*d* on the circumference of the connecting end arrangement plate 153 travels sequentially one by one between the two discs 254*a*, 254*b* along the radial direction, is provided so that the center of the reflecting surface is situated at the position corresponding to the radius of the circumference of the connecting end arrangement plate. Further, the reflecting surface of the reflecting prism 155 sequentially receives each light traveling downward from the connecting ends 153*a* to 153*d* at an incidence angle of 45 degrees, and reflects it to travel along the radial direction. For achieving this, it is provided so that the normal direction of reflecting surface of the reflecting prism 155 forms an angle of 45 degrees or 135 degrees with respect to the normal direction (rotation axial line direction) of the disc surface of the light guiding rotary plate for light reception selection 254.

On the hole in the center of the lower disc 254*b* of the light guiding rotary plate 254, reflecting prism 160 is provided so that the rotation axial line penetrates the center of the reflecting surface of the reflecting prism 160. The reflecting surface of the reflecting prism 160 sequentially receives the light from the reflecting prism 155 at an incidence angle of 45 degrees, and reflects to travel downward approximately along the rotation axial line of the light guiding rotary plate 254. For achieving this, it is arranged so that the normal direction of the reflecting surface of the reflecting prism 160 forms 45 degrees or 135 degrees with respect to the normal direction (rotation axial line direction) of the disc surface of the light guiding rotary plate for light reception selection 254, while it is parallel with the reflecting surface of the reflecting prism 155.

Here, the reference numeral 461 is a motor for rotating the light guiding rotary plate 254, which rotationally drives the light guiding rotary plate 254 via a timing belt 481 hung across the rotation axis 159 and a drive axis 471 of the motor 461. At the position corresponding to the rotation axis 159 in a partition wall 411 partitioning between a dark room 241*a* and a dark room 241*b*, a hole 413 allowing transmission of light is pierced.

As shown in FIG. 10(*a*), the dark room 241*b* is provided with an optical filter arrangement plate 156 formed with a plurality of optical filters that are movable with respect to the rotation axial line so as to allow sequential transmission of the light outgoing from the light guiding rotary plate 254 having passed through the hole 413.

As shown in FIGS. 10(*a*) and 10(*b*), the optical filter arrangement plate 156 has a plurality of (four, in this example) optical filters 761 to 764 arranged along the circumference so that the centers thereof intersect with the rotation axial line at a right angle, and rotates about a rotation axial line that is concentric with the circumference. In the drawing, the reference numeral 462 is a motor for rotating the optical filter arrangement plate 156, which rotationally drives the optical filter arrangement plate 156 via a timing belt 482 hung across the rotation axis 159 of the arrangement plate 156 and a drive axis 472 of the motor 462. In a partition wall 412 partitioning between the dark room 241*b* and the dark room 241*c*, a hole 414 having substantially the same diameter with the hole 413 is pierced at the position corresponding to the hole 413 through which a rotation axial line of the light guiding rotary plate 254 penetrates.

As shown in FIG. 10(*a*), the dark room 241*c* is provided with the photoelectric unit 150 into which the light having passed both each of the connecting ends 153*a* to 153*d* and the optical filters 761 to 764 is introduced. The photoelectric unit 150 corresponds to a photoelectric element.

Figure 11:
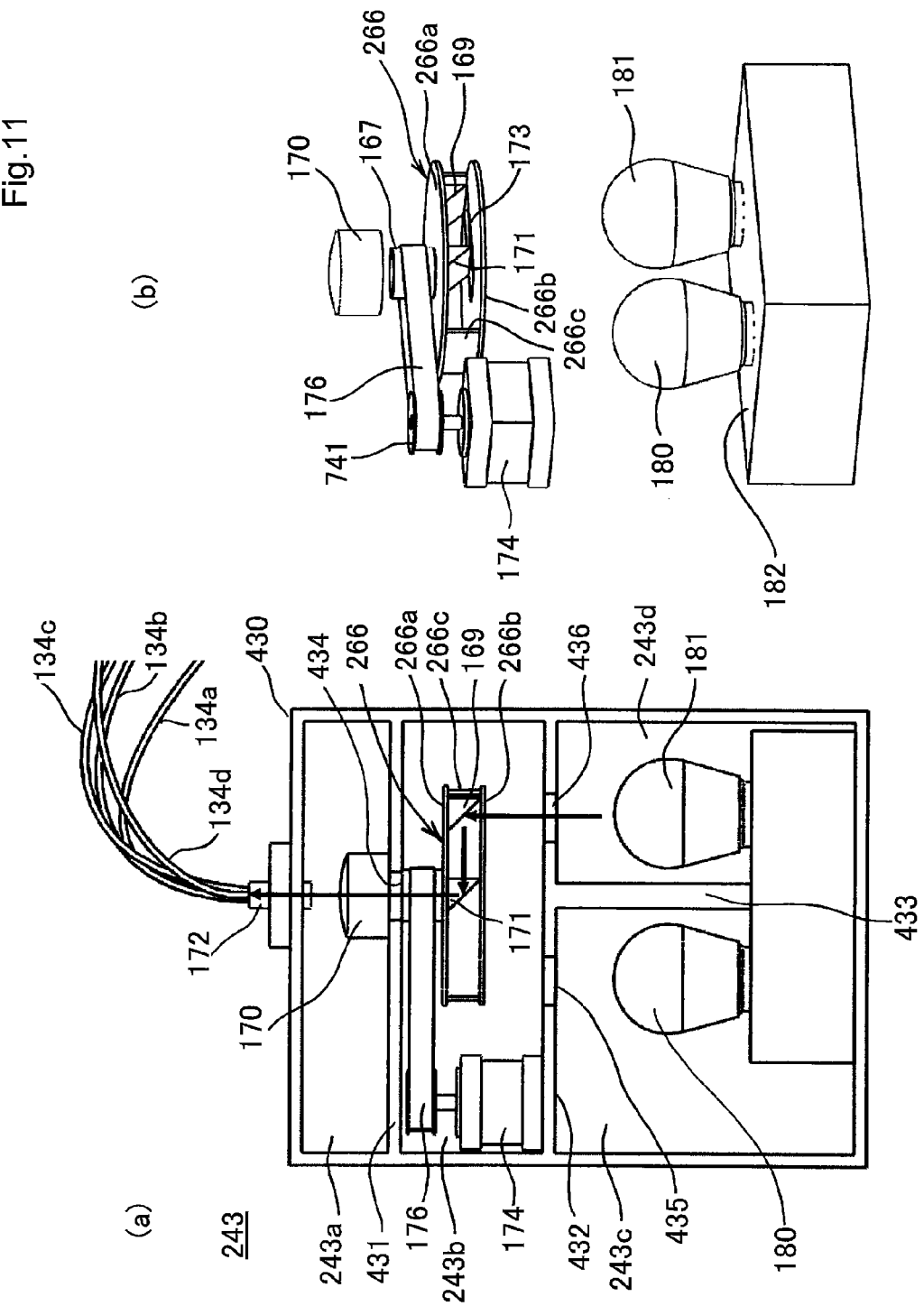
FIG. 11 is a partially cutaway lateral view and a partial perspective view of the light source selecting unit of FIG. 8.

FIG. 11 is a view showing the light source selecting unit 243.

As shown in FIG. 11(*a*), in the light source selecting unit 243, an optical system is accommodated in a box body 430 that is partitioned into four rooms 243*a*, 243*b*, 243*c*, 243*d* by partition plates 431, 432, 433. To a top plate of the box body 430, a connector 172 in which connecting ends on the opposite side of the light emitting ends of the light emitting optical fibers 134*a* to 134*d* are circularly converged with a certain area with respect to the connecting end of the light source selecting unit 243 is attached so that it penetrates the top plate.

As shown in FIGS. 11(*a*) and 11(*b*), bulb-type light sources 180, 181 having predetermined different exciting wavelengths such as a xenon lamp or a halogen lamp are respectively provided in the rooms 243c, 243d. The partition plate 432 partitioning the rooms 243c, 243d respectively accommodating the light sources 180, 181 from the room 243b is pierced with circular output holes 435, 436 for outputting the light of the light source for each light source 180, 181. The reference numeral 182 is a light source arrangement part corresponding to a light source arrangement plate in which the light sources 180, 181 are arranged.

As shown in FIGS. 11(a) and 11(b), the room 243b is provided with a light guiding rotary plate 266 serving as the light source selecting part, that is provided to be rotatable concentrically with the circumference passing respective centers of the circular output holes 435, 436 (or respective centers of the light source 180 and the light source 181) and sequentially guides the light outgoing from the output holes 435, 436 independently to outgo approximately along the rotation axial line.

As shown in FIGS. 11(a) and 11(b), the light guiding rotary plate 266 has two discs 266a, 266b and a spacer 266c, and an optical system is provided in such a manner that it is sandwiched by the two discs 266a, 266b up and down. The lower disc 266b is pierced with rectangular a hole 173 along the radius of the disc 266b, and the center of the upper disc 266a is connected with a rotation axis 167 having a tubular shape pierced with a circular hole that is concentric with the rotation axial line through which the light can transmit approximately along the rotation axial line.

Below the upper disc 266a, one reflecting prism 169 having a reflecting surface provided to allow the light from each of the output holes 435, 436 to travel sequentially one by one between the two discs 266a, 266b along the radial direction, is provided so that center of the reflecting surface is situated at the position corresponding to the radius of the circumference passing the output holes 435, 436. Further, the reflecting surface of the reflecting prism 169 sequentially receives the light traveling upward from the output holes 435, 436 from each of the light sources 180, 181 at an incidence angle of 45 degrees, and reflects it to travel along the radial direction. For achieving this, it is provided so that the normal direction of the reflecting surface of the reflecting prism 169 forms an angle of 45 degrees or 135 degrees with respect to the normal direction (rotation axial line direction) of the disc surface of the light guiding rotary plate for light source selection 266.

Under the center hole of the upper disc 266a of the light guiding rotary plate 266, reflecting prism 171 is provided so that the rotation axial line penetrates the center of the reflecting surface of the reflecting prism 171. The reflecting surface of the reflecting prism 171 sequentially receives the light from the reflecting prism 169 at an incidence angle of 45 degrees, and reflects it to travel upward approximately along the rotation axial line of the rotary plate 266. For achieving this, it is arranged so that the normal direction of the reflecting surface of the reflecting prism 171 forms 45 degrees or 135 degrees with respect to the normal direction (rotation axial line direction) of the disc surface of the light guiding rotary plate for light source selection 266, while it is parallel with the reflecting surface of the reflecting prism 169.

Here, the reference numeral 174 is a motor for rotating the light guiding rotary plate 266. The motor rotationally drives the light guiding rotary plate 266 via a timing belt 176 hung between the rotation axis 167 and a drive axis 741 of the motor 174. At the position corresponding to the rotation axis 167 in the partition wall 431 partitioning between the room 243a and the room 243b, a circular hole 434 allowing transmission of light is pierced.

As shown in FIG. 11(a), the room 243a is provided with a focused parallel light lens 170 capable of emitting focused parallel light toward the connector 172. The focused parallel light lens 170 is provided on the hole 434, and the hole 434 is larger than the section area of the connector 172, but has a diameter smaller than that of the focused parallel light lens 170.

Next, an operation of the optical fiber measurement device 200 according to the third embodiment will be described. The micro plate 112 where ninety-six wells 113 holding a reaction solution containing a fluorescent substance applied by a dispenser in advance are arranged along a flat face is covered with a film, and loaded in the optical fiber measurement device 200.

The loaded micro plate 112 is shifted in the X-axis direction by the X-axis shifting mechanism, and the fixed four measurement ends 125a to 125d are positioned on the first line of the micro plate 112, and by the Y-axis shifting mechanism, the measurement ends 125a to 125d are positioned closely above the film over four wells 113 every other line along the column direction of the wells 113 on the first line, and through the film, and through the light emitting optical fibers 134a to 134d of the measurement ends 125a to 125d, the light from the bulb-type light source 180 is selected by rotating the light guiding rotary plate for light source selection 266 and situating the reflecting prism 169 above the hole 435, and a beam of excitation light is emitted inside each of the wells 113 through the film via the focused parallel light lens 170. By rotating the optical filter arrangement plate 156 by 360 degrees in sequentially outputting the fluorescence for each well 113 approximately along the central rotation axial line by receiving fluorescence outgoing from the well 113 in response to emission of the excitation light by the measurement ends 125a to 125d and transmitting it through the light receiving optical fibers 132a to 132d, and processing by rotating the light guiding rotary plate for light reception selection 254 provided in the light reception selecting unit 241 by 90 degrees, for example, for 50 milliseconds and stopping for 50 milliseconds, sixteen kinds of light having wavelengths sequentially passed through four kinds of optical filters 761 to 764 are obtained and sequentially introduced into the photoelectric unit 150. By conducting the process of 4×100 milliseconds for the four light receiving optical fibers 132a to 132d, it takes 1.6 second. In case of necessity, a similar process is conducted while selecting the light source 181 by situating the reflecting prism 169 above the hole 436 by rotating the light guiding rotary plate for light source selection 266 by 180 degrees from the aforementioned position.

As the next step, by shifting the micro plate 112 by one pitch in the Y-axis direction by the Y-axis shifting mechanism (for example, a timing belt, a motor) with respect to the fixed measurement ends 125a to 125d, the aforementioned process is repeated while it is positioned closely above the film over other four wells 113 situated every other line in eight wells 113 on the first line of the micro plate 112. Therefore, it takes 1.6 second (when only the light source 180 is selected) as described above.

Next, by shifting the micro plate 112 by one line along the X-axis direction by means of the X-axis shifting mechanism (for example, a timing belt, a motor), it is possible to position it on the second line of the micro plate 112. For each well 113 on the second line, the measurement process is sequentially conducted in a similar manner. In a similar manner, the process is conducted for the total of twelve lines. Accordingly, the entire process takes, for example, 3.2×12=38.4 seconds excluding the time required for shifting between wells (when only the light source 180 is selected).

According to the device of the third embodiment, the light from the light receiving optical fibers can be directly guided approximately along the central axis although it is necessary to provide both the light guiding rotary plate and the optical filter arrangement plate movable independently, so that it is possible to reduce the number of components of the optical system without interposition of a focusing lens and to conduct measurement in a clear state while keeping the light quantity of the light. Also, the light guiding rotary plate has a simple structure and is easy to be produced.

According to the device of the third embodiment, in accommodating an optical system, since the optical system is accommodated in a plurality of rooms formed by partitioning a box by a wall depending on the optical system and the rooms are mutually connected via a hole through which light can transmit, it is possible to form a rigid and highly reliable simple structure.

Figure 12:
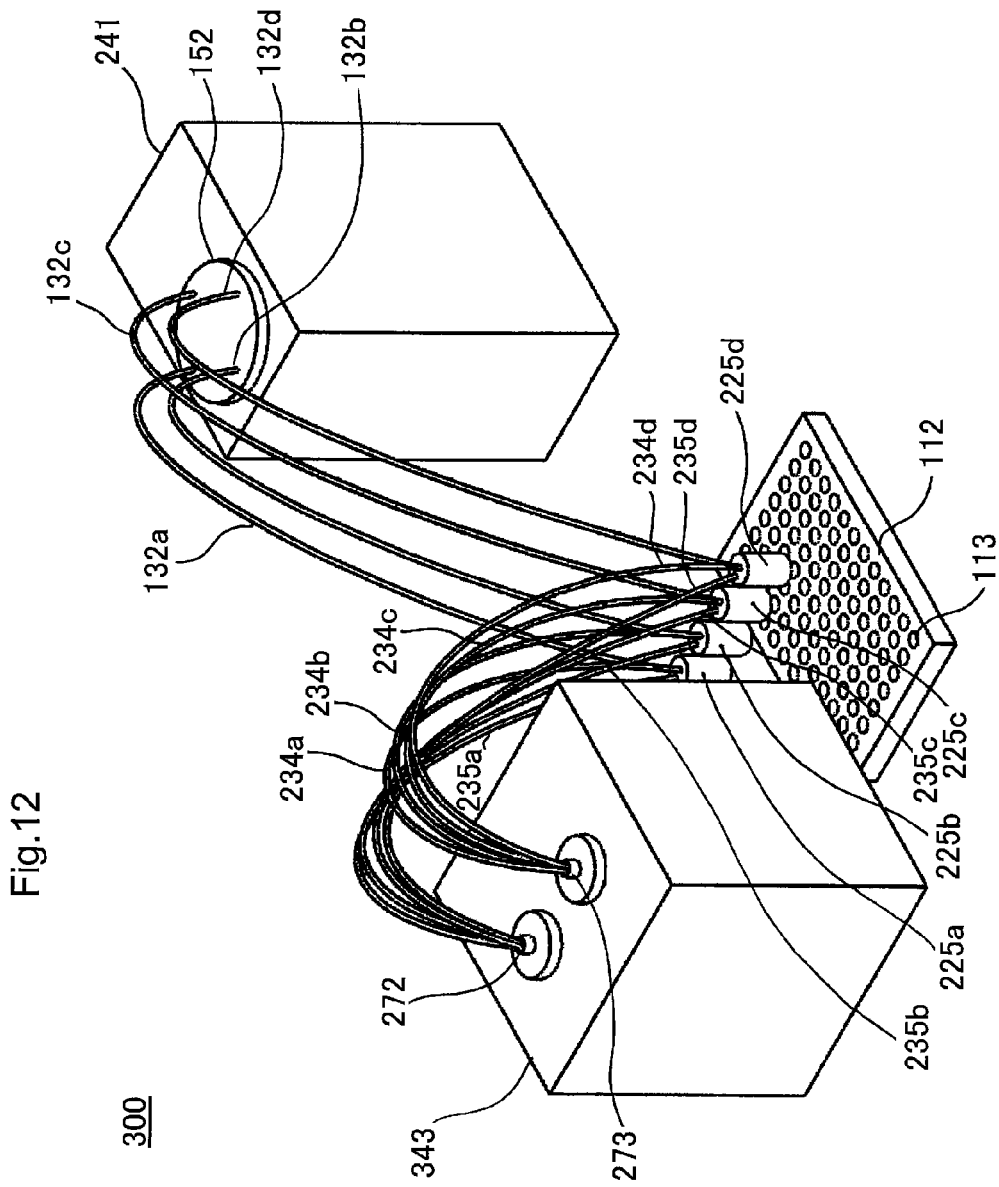
FIG. 12 is a perspective view showing a primary part of an optical fiber measurement device according to a fourth embodiment of the present invention.
Figure 13:
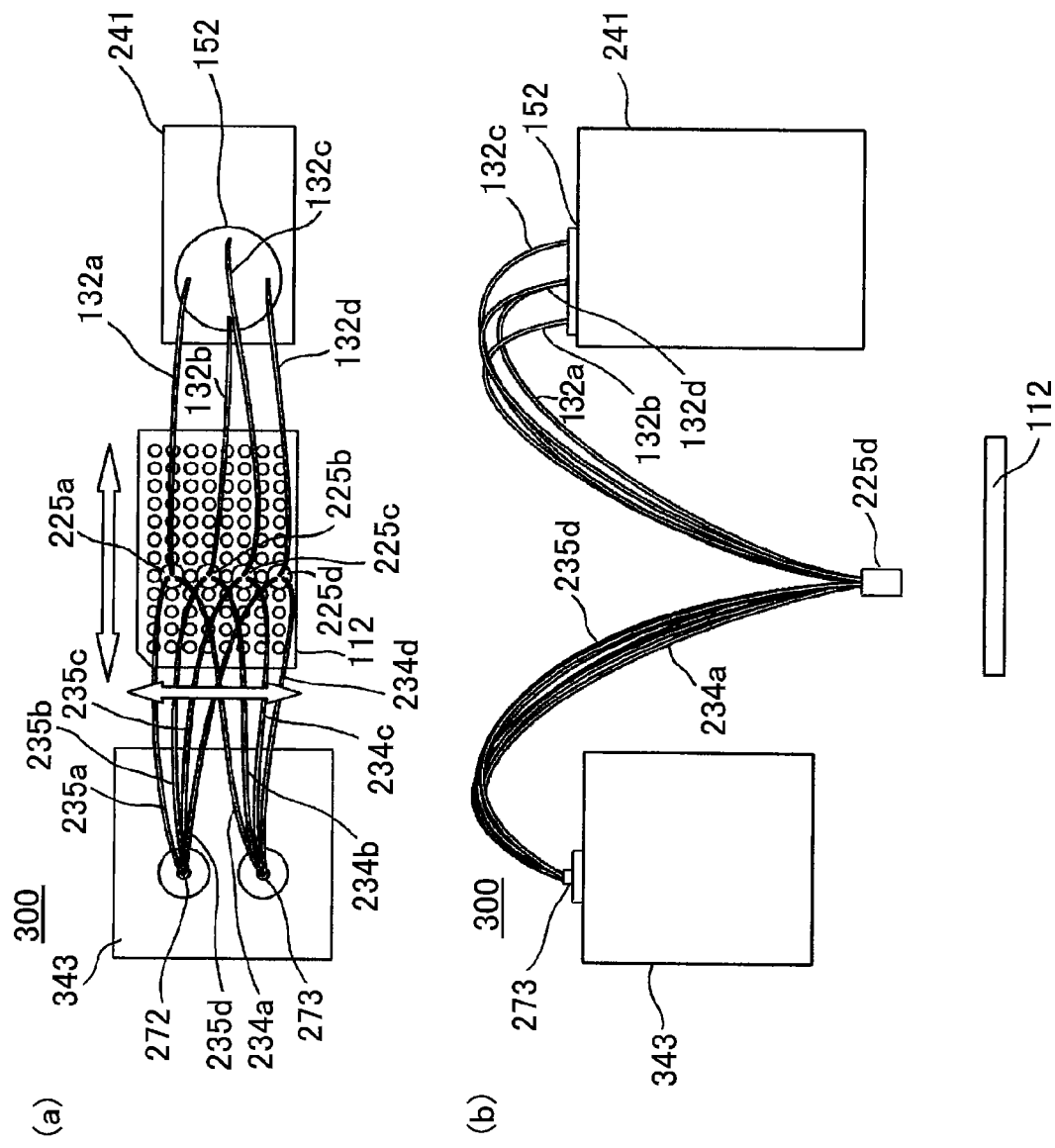
FIG. 13 is a plan view and a front view of a primary part shown in FIG. 12.

Next, a primary part of an optical fiber measurement device 300 according to a fourth embodiment is shown in FIGS. 12 and 13. The one identical to that shown in FIGS. 8 to 11 is denoted by the same reference numeral, and description thereof will not be repeated. The device 300 has a micro plate 112 serving as the planar liquid holder in which a plurality of (8×12=96, in this example) wells 113 as liquid holding portions capable of holding a PCR reaction solution containing a fluorescent substance are arranged along a flat face.

On the micro plate 112, four measurement ends 225a, 225b, 225c, 225d, as those corresponding to a measurement head, are provided fixedly to the substrate of the device. These four measurement ends 225a to 225d are arranged at such an interval (18 mm pitch, in this example) that they are above plural wells 113, for example, four wells 113 arranged every other well among eight wells 113 on one line of the micro plate 112.

Each of the measurement ends 225a to 225d is optically connected with respective one pair of a light receiving end which is one end of each light receiving optical fiber 132a to 132d and a light emitting end which is one end of each light emitting optical fiber 134a to 134d and each light emitting optical fiber 135a to 135d, and a connecting end which is the other end of each light receiving optical fiber 132a to 132d is optically connected with a light reception selecting unit 241 (and a photoelectric unit 150 corresponding to a photoelectric element) corresponding to a light reception selecting element, and a connecting end which is the other end of each light emitting optical fiber 134a to 134d and a connecting end which is the other end of each light emitting optical fiber 135a to 135d are optically connected with a light source selecting unit 343 corresponding to a light source selecting element.

Since the measurement head is fixed, shifting of the micro plate 112 serving as the planar liquid holder is as same as that in the third embodiment, and hence description thereof will not be repeated. Also the light reception selecting unit 241 is as same as that of the third embodiment, and hence description thereof will not be repeated.

On the other hand, the light source selecting unit 343 will be described by using FIGS. 12 to 14 because it is different from that of the third embodiment.

As shown in FIGS. 12 to 13, in the optical fiber measurement device 300 according to the fourth embodiment, four light emitting optical fibers 234a to 234d are connected at a connecting end on the opposite side of the light emitting end with a connector 272 of the light source selecting unit 343, and the four light emitting optical fibers 235a to 235d are connected at a connecting end on the opposite side of the light emitting end with a connector 273 of the light source selecting unit 343.

Figure 14:
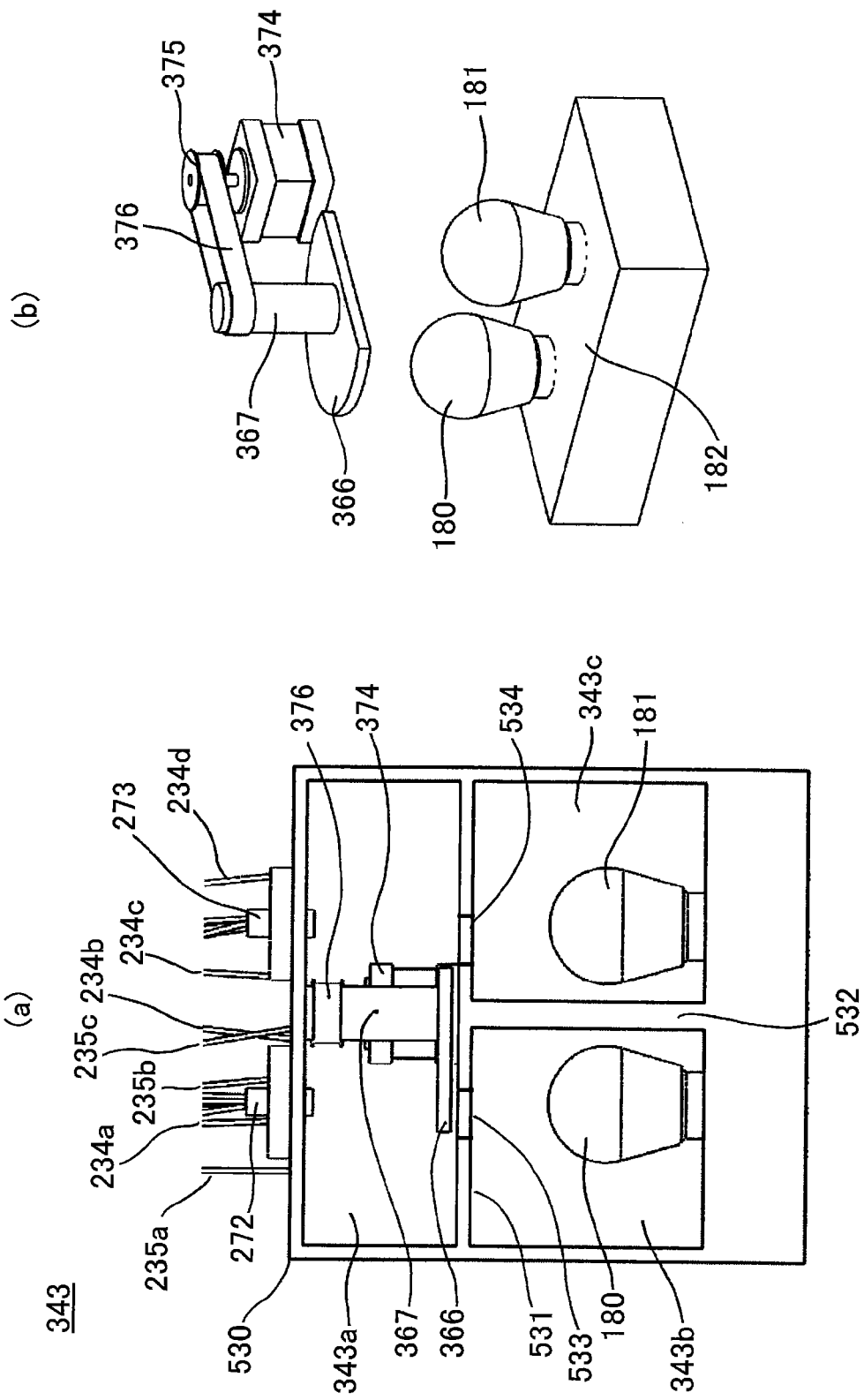
FIG. 14 is a partially cutaway lateral view and a partial perspective view of a light source selecting unit of FIG. 12.

FIG. 14 is a view showing the light source selecting unit 343.

As shown in FIG. 14(a), in the light source selecting unit 343, an optical system is accommodated in a box body 530 that is partitioned into three rooms 343a, 343b, 343c by partition plates 531, 532. To a top plate of the box body 530, the connector 272 in which connecting ends on the opposite side of the light emitting ends of the light emitting optical fibers 234a to 234d are circularly converged with a certain area, and the connector 273 in which connecting ends on the opposite side of the light emitting ends of the light emitting optical fibers 235a to 235d are circularly converged with a certain area are attached to penetrate the top plate.

As shown in FIGS. 14(a) and 14(b), bulb-type light sources 180, 181 are provided respectively in the rooms 343b, 343c. The partition plate 531 partitioning the rooms 343c, 343d respectively accommodating the light sources 180, 181 from the room 343a is pierced with circular output holes 533, 534 for outputting the light of the light source for each light source 180, 181. As an optical system for light emission, the room 343a is provided so that light of the light sources 180, 181 passing through the circular output holes 533, 534 is at a position where light emission on the connectors 272, 273 is possible.

As shown in FIGS. 14(a) and 14(b), the room 343a is provided with a light source selecting part having an approximately hemi-circular shielding plate 366 provided to be rotatable concentrically with the circumference passing respective centers of circular output holes 533, 534 (or respective centers of the light source 180 and the light source 181), for sequentially covering either one of the output holes 533, 534 and sequentially shielding the light from the light source 180 or the light source 181 with respect to the connectors 272, 273, a rotation axis 367 rotating the shielding plate 366 every 180 degrees of central degree, and a motor 374 for rotationally driving the rotation axis 367. Here, the reference numeral 376 is a timing belt hung across a motor axis 375 of the motor 374 and the rotation axis 367.

Next, an operation of the optical fiber measurement device 300 according to the fourth embodiment will be described. The micro plate 112 where ninety-six wells 113 holding a reaction solution containing a fluorescent substance applied by a dispenser in advance are arranged along a flat face is covered with a film, and loaded in the optical fiber measurement device 300.

The loaded micro plate 112 is shifted in the X-axis direction by the X-axis shifting mechanism, and the fixed four measurement ends 225a to 225d are positioned on the first line of the micro plate 112, and by the Y-axis shifting mechanism, the measurement ends 225a to 225d are positioned closely above the film over four wells 113 situated every other line along the column direction of the wells 113 on the first line, and through the film, and through the light emitting optical fibers 234a to 234d and the light emitting optical fibers 235a to 235d of the measurement ends 225a to 225d, the light from the bulb-type light source 180 is selected and emitted by the light source selecting part, by rotating the hole 534 outputting the light from the light source 181 to the position covered with the shielding plate 366. Fluorescence outgoing from the well 113 in response to emission of the excitation light is received by the measurement ends 225a to 225d, and transmitted through the light receiving optical fibers 132a to 132d, and the light receiving process is conducted by the light reception selecting unit 241 as described in the third embodiment.

Similarly, in case of necessity, by emitting light mainly on the connector 273 by rotating, as the light source selecting part, the shielding plate 366 by 180 degrees from the position to be positioned to cover the hole 533 to select the light source 181, light is emitted inside the well 113 through the measurement ends 225a to 225d, and a similar process is repeated.

As the next step, by shifting the micro plate 112 by one pitch in the Y-axis direction by the Y-axis shifting mechanism with respect to the fixed measurement ends 225a to 225d, the aforementioned process is repeated while it is positioned closely above the film over other four wells 113 situated every other line in eight wells 113 on the first line of the micro plate 112.

Further, by shifting the micro plate 112 by one line along the X-axis direction using the X-axis shifting mechanism, it can be positioned on the second line of the micro plate 112. For each well 113 on the second line, the measurement process is sequentially conducted in a similar manner. The process is conducted for all of the twelve lines.

The foregoing embodiments described above are concrete explanations given for better understanding of the present invention, and will not limit other embodiments. Therefore, they may be modified within the range not changing the subject matter of the present invention. For example, in the foregoing embodiment, while only the case having 12×8 or 8×12 (9 mm pitch) wells as a the micro plate, and the case having six or four the measurement ends are described (the number (n) of optical fiber bundles or connecting ends is six in the first or second embodiment, and four in the third or fourth embodiment), the invention is not limited by these numerical values, and the case providing a measurement end for every liquid holding portion is also possible. The description is made only for the case where the connecting ends are arranged on the connecting end arrangement plate at a central angle of 60 degrees, the number (m) of the optical filters of the light reception selecting element is three, the central angles of the optical filters are 100 degrees, 100 degrees and 160 degrees, however, the invention will not be limited to these numerical values. The present invention may be applied for the cases of various numerical values using the forgoing mathematical formula or the like.

In the example of the first or second embodiment, the magnitude of a central angle of neighboring connecting ends on the connecting end arrangement plate is an angle obtained by equally dividing 360 degrees, however, the optical filters may be arranged at a neighboring central angle of an angle obtained by equally dividing 360 degrees, vice versa.

As to the micro plate, while the description is made for the case of eight rows×twelve columns or twelve rows×eight columns in a pitch of 9 mm, it goes without saying that the present invention may be applied to various micro plates, for example, a micro plate having sixteen columns×twenty four rows in a pitch of 4.5 mm, and other micro plates having twelve rows×sixteen columns, six rows×eight columns and the like various pitches without limited to the above case. Other numerical values of size, number, angle, predetermined time, life time of fluorescence, predetermined connecting time and so on are given for exemplification, and it goes without saying that the present invention is not limited to these numerical values.

As to the light reception selecting element, and the light source selecting element, the number of connecting ends, the number or presence or absence of optical filter, and the number of bundles of connecting ends are not limited to those described above.

The spatial representations such as X-axis, Y-axis, Z axis, vertical direction, lateral direction, up and down, row and column and so on are given for the purpose of exemplification and are not intended to limit spatial direction and position of the structure.

INDUSTRIAL APPLICABILITY

The present invention relates to an optical fiber measurement device and method, and is usable in various fields including biochemical field, agricultural field, pharmaceutical field, medical field, industrial field and the like where, for example, a DNA which is an initial template of PCR is quantified by monitoring nucleic acid (DNA) amplified by PCR requiring temperature control in real time, and using an amplification curve of the obtained PCR product, or various reactions not requiring temperature control are conducted.

REFERENCE SIGNS LIST 10, 100, 200, 300 optical fiber measurement device
12, 112 micro plate (planar liquid holder)
13, 113 well (liquid holding portion)
20a to 20f optical fiber bundle
25a to 25f, 125a to 125d, 225a to 225d measurement ends
32a to 32f, 132a to 132d light receiving optical fibers
34a to 34f, 134a to 134d, 135a to 135d light emitting optical fibers
40 measurement head
41, 141 light reception selecting element
241 light reception selecting unit (corresponding to light reception selecting element)
43, 143 light source selecting element
243, 343 light source selecting unit (corresponding to light source selecting element)
50 photoelectric element
150 photoelectric unit (corresponding to photoelectric element)

The invention claimed is:

1. An optical fiber measurement device comprising:
a planar liquid holder having a plurality of liquid holding portions capable of holding a reaction solution containing a fluorescent substance arranged along a flat face;
a plurality of light receiving optical fibers for transmitting fluorescence generated in the liquid holding portions;
a plurality of light emitting optical fibers for transmitting excitation light into the liquid holding portions;
a measurement head capable of being positioned in the entire or part of the plurality of liquid holding portions of the planer liquid holder while supporting a plurality of measurement ends having a bundle of one light receiving end of the light receiving optical fibers receiving the fluorescence and one or two or more light emitting ends of the light emitting optical fibers emitting the excitation light;
a light reception selecting element that, by sequentially selecting one by one from the plural light receiving optical fibers and sequentially selecting one by one from plural kinds of wavelength or wavelength bands, sequentially guides light of the selected wavelength or wavelength band of the fluorescence received by the selected light receiving optical fibers to one photoelectric element; and
a photoelectric element for sequentially conducting photoelectric conversion on the fluorescence that is selected by the light reception selecting element and guided,
wherein the light reception selecting element has:
a connecting end arrangement plate supporting a plurality of connecting ends on the opposite side of the light receiving ends of the light receiving optical fibers arranged along a circumference at a predetermined central angle;

a light receiving rotary plate provided oppositely, closely to the connecting end arrangement plate and provided to be rotatable concentrically with the circumference of the connecting end arrangement plate;

a plurality of optical filters that are arranged on the light receiving rotary plate at a predetermined central angle along a circumference that has a same diameter with the circumference of the connecting end arrangement plate and is concentric therewith, and are optically connectable one by one with each connecting end by rotation of the light receiving rotary plate; and a light receiving optical system provided in the light receiving rotary plate, for allowing light passing each of the optical filters independently enter a central axis region of the light receiving rotary plate, and the photoelectric element is provided to allow introduction of the light entering the central axis region.

2. The optical fiber measurement device according to claim 1, wherein the central angle of the connecting end and the central angle of the optical filter are defined so that during rotation of a total of 360 degrees by repetition of rotation in a constant direction by an equivalent angle of the light receiving rotary plate and stopping for a predetermined connecting time, every combination of all of the connecting ends provided in the connecting end arrangement plate and all of the optical filters provided in the light receiving rotary plate is optically connected one by one for the predetermined connecting time, and the light having passed both the connecting end and the optical filter is guided to the photoelectric element.

3. The optical fiber measurement device according to claim 1, further comprising a shifting mechanism that allows relative movement between the measurement head supporting the measurement ends and the planar liquid holder.

4. The optical fiber measurement device according to claim 1, comprising an exciting light source selecting element, for selecting light from a light source for the excitation light and guiding it to connecting ends on the opposite side of the light emitting ends of one or two or more the light emitting optical fibers.

5. The optical fiber measurement device according to claim 4, wherein the exciting light source selecting element has:

an exciting light source arrangement plate provided with arranged plural kinds of exciting light sources;

a light source selecting part for selecting one of the exciting light sources arranged in the exciting light source arrangement plate; and a light emitting optical system for guiding light from the exciting light source selected by the light source selecting part to one or two or more bundles of the connecting ends on the opposite side of the light emitting ends of the light emitting exciting optical fibers.

6. The optical fiber measurement device according to claim 5, wherein the exciting light source arrangement plate supports a plurality of exciting light sources arranged along a circumference at a predetermined central angle, the light source selecting part and light emitting optical system are a light guiding rotary plate for light source selection that is provided oppositely to the exciting light source arrangement plate and provided to be rotatable concentrically with the circumference of the exciting light source arrangement plate, and guides the light entered from the light source to outgo approximately along its rotation axial line, and the bundles of the connecting ends of the light emitting optical fibers are provided so that the rotation axial line penetrates therethrough.

7. The optical fiber measurement device according to claim 5, wherein the exciting light source arrangement plate supports a plurality of exciting light sources arranged along circumference at a predetermined central angle, the light source selecting part selects one from the plural light sources provided in the exciting light source arrangement plate and allows passing of the light of the light source, while shielding light from other light sources, and the light emitting optical system is a box body through which the light from the light source can pass, where each bundle of the connecting ends of the plural light emitting optical fibers are arranged at a position to which the light from the corresponding exciting light source can be directly emitted.

8. The optical fiber measurement device according to claim 2, comprising an exciting light source selecting element, for selecting light from a light source for the excitation light and guiding it to connecting ends on the opposite side of the light emitting ends of one or two or more the light emitting optical fibers.

* * * * *